(12) United States Patent
Vrijbloed et al.

(10) Patent No.: US 8,796,183 B2
(45) Date of Patent: Aug. 5, 2014

(54) TEMPLATE FIXED BETA-HAIRPIN LOOP MIMETICS AND THEIR USE IN PHAGE DISPLAY

(75) Inventors: Jan Wim Vrijbloed, Zürich (CH); Daniel Obrecht, Blättwil (CN); Sergio Locurio, Küsnacht (CH); Frank Otto Gombert, Huttingen (DE); Christian Ludin, Aesch (CH); Françoise Jung, Zürich (CH)

(73) Assignees: Polyphor Ltd., Allschwil (CH); Universität Zürich, Zürich (CH)

( * ) Notice: Subject to any disclaimer, the term of this patent is extended or adjusted under 35 U.S.C. 154(b) by 82 days.

(21) Appl. No.: 13/196,712

(22) Filed: Aug. 2, 2011

(65) Prior Publication Data
US 2011/0319291 A1    Dec. 29, 2011

Related U.S. Application Data

(62) Division of application No. 10/579,104, filed as application No. PCT/EP03/12783 on Nov. 15, 2003, now Pat. No. 7,994,118.

(51) Int. Cl.
*C40B 30/04* (2006.01)
*C07K 5/00* (2006.01)

(52) U.S. Cl.
USPC .................. 506/9; 506/7; 530/326; 530/327; 530/300

(58) Field of Classification Search
USPC ......................... 506/9, 7; 530/326, 327, 300
See application file for complete search history.

(56) References Cited

U.S. PATENT DOCUMENTS

| 6,878,804 | B1 * | 4/2005 | Robinson et al. | 530/317 |
| 7,229,777 | B2 * | 6/2007 | Cochran et al. | 435/7.1 |
| 7,253,146 | B2 * | 8/2007 | Obrecht et al. | 424/433 |
| 7,413,537 | B2 * | 8/2008 | Ladner et al. | 506/14 |
| 2003/0036093 | A1 * | 2/2003 | Floudas et al. | 435/7.1 |

FOREIGN PATENT DOCUMENTS

| WO | 00/62815 A2 | 10/2000 |
| WO | 00/77194 A1 | 12/2000 |
| WO | 03/054000 A1 | 7/2003 |

OTHER PUBLICATIONS

Dimarcq et al.; Cysteine-Rich Antimicrobial Peptides in Invertebrates; Biopolymers (Peptide Science), vol. 47, pp. 465-477; 1998.
Lowman; Bacteriophage Display and Discovery of Peptide Leads for Drug Development; Annu. Rev. Biophys. Biomol. Struct. 1997; vol. 26, pp. 401-424; 1997.
Shankaramma et al.; Macrocyclic Hairpin Mimetics of the Cationic Antimicrobial Peptide Protegrin I: A New Family of Broad-Spectrum Antibiotics; ChemBioChem; vol. 3, pp. 1126-1133; 2002.
Skelton et al.; Amino Acid Determinants of β-Hairpin Conformation in Erythropoeitin Receptor Agonist Peptides Derived from a Phage Display Library; J. Mol. Biol.; vol. 316, pp. 1111-1125; 2002.
Wrighton et al.; Small Peptides as Potent Mimetics of the Protein Hormone Erythropoietin; Science; vol. 273, pp. 458-463, Jul. 26, 1996.

* cited by examiner

*Primary Examiner* — Teresa Wessendorf
(74) *Attorney, Agent, or Firm* — Hoffmann & Baron, LLP

(57) ABSTRACT

A method of screening for template-fixed β-hairpin mimetics and libraries including a plurality of these mimetics is provided. The template-fixed β-hairpin mimetics are of the following general formula:

$$R^1\text{-Cys-Z-Cys-}R^2 \qquad\qquad\qquad \text{I}$$

wherein the two cysteine residues are bridged by a disulfide bond, thereby forming a cyclic peptide; $R^1$ and $R^2$ are di- or tripeptide moieties of certain types, as defined herein; and Z is a chain of n amino acid residues with n being an integer from 4 to 20 and with each of these n amino acid residues being, independently, derived from any naturally occurring L-α-amino acid.

3 Claims, 4 Drawing Sheets

TEMPLATE FIXED BETA-HAIRPIN LOOP MIMETICS AND THEIR USE IN PHAGE DISPLAY

CROSS-REFERENCE TO RELATED APPLICATIONS

This application is a divisional of U.S. application Ser. No. 10/579,104, filed May 12, 2006, and afforded a date of receipt of 35 U.S.C. 371(c)(1), (c)(2), and (c)(4) requirements of Nov. 2, 2006, which U.S. application Ser. No. 10/579,104, now U.S. Pat. No. 7,994,118, is the national phase in the U.S. of International Application No. PCT/EP2003/012783, filed Nov. 15, 2003, the entire contents of all of which are incorporated by reference herein.

FIELD OF THE INVENTION

The present invention relates to compositions and methods of certain peptide sequences consisting of residues of naturally occurring L-α-amino acids wherein certain amino acid residues, depending on their positions in the chains, are cysteines which are bridged by a disulfide bond, thereby forming cyclic peptides, and certain other amino acid residues which are adjacent to the said cysteines form di-or tripeptide moieties of certain types, as defined herein below, which together act as templates in order to facilitate the formation and stabilization of β-hairpin loop structures. By virtue of their stability and constraints these template fixed hairpin loop mimetics can exhibit higher or prolonged activity against protein binding partners.

The templates can be transplanted into the construction of phage display derived hairpin loop mimetics for library screening and drug screening. Methods and compositions of the present invention are useful for screening and identifying interacting proteins in vitro. The present invention can serve as an additional efficient lead finding tool for targets where it is difficult to transfer protein epitopes from into small peptides or peptide mimetics.

BACKGROUND OF THE INVENTION

The surface loops of proteins and bioactive peptides have often been implicated in recognition by protein binding partners. Accordingly, it is of interest to investigate these loops as potential leads for drug discovery. Particularly of interest are β-hairpins: The β-hairpin motif is very abundant in nature and occurs on the surface of many protein ligands and in the hypervariable domains of antibodies. The β-hairpin motif consists of two antiparallel β-strands linked by a short loop or turn and have been classified depending on the H-bonding network [Sibanda, B. L.; Blundell, T. L.; Thornton, J. M. *J. Mol. Biol.* 1989, 206, 759-777].

The ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). However these molecules may not be synthesized in libraries as large as $10^{10}$ or $10^{12}$.

A complementary strategy for peptide-based lead discovery consists of display of libraries on filamentous bacteriophage which allows the preparation of libraries as large as $10^{10}$-$10^{12}$, many magnitudes larger than libraries that may be prepared synthetically.

Furthermore rapid and inexpensive selection protocols are available for identifying those library members that bind to a target of interest. Phage display technique allows the construction of cyclic constrained peptides such as disulfide-constrained β-hairpin loops, as is well known (H. B. Lowman, *Annu. Rev. Biophys. Biomol. Struct.* 1997, 26, 401-24).

These loops represent a limited number of conformations which may result in isolation of affinity ligands for a receptor target. Cyclic peptides, however, stabilized by only one disulfide bond are still conformationally quite flexible. Also, it is well known that disulfide bond formation and cleavage can be reversible and flexibility is increased by the fact that the peptide constraints are fused to the amino terminus of the gene III protein. Thus it is important to stabilize such loop constructs by additional residues, adjacent to the disulfide bond which favor the β-sheet conformation. (R. H. Hoess, *Current opinion in Structural Biology* 1993, 3, 572-579). This may not lead to high affinity ligands for a receptor target. The same peptide loop is fixed in the natural protein scaffold by the protein scaffold on to N- and C-terminus of the loop and is additionally constrained by hydrogen bonds of anti-parallel beta-sheets which is induced by the natural protein scaffold. Other approaches have been proposed such as peptide scaffolds for turn display (A. G. Cochran, R. T. Tong, M. A. Starvasnik, E. J. Park, R. S. McDowell, J. E. Theaker, N. J. Skeleton, *J. Am. Chem. Soc.* 2001, 123, 625-632). Another possible solution to this problem is to use structural constraints of a folded protein to present small variable peptide segments (P.-A. Nygren, M. Uhlen, *Curr. Opin. Struc. Biol.* 1997, 7, 463-469; G. P. Smith, S. U. Patel, J. D. Windass, J. M. Thornton, G. Winter, A. D. Griffiths, *J. Mol. Biol.* 1998, 277, 317-332; A. Christmannn, K. Walter, A. Wenzel, R. Krazner, R. Kolmar, *Protein Eng.* 1999, 12, 797-806).

In fact the epitope transfer from proteins into small peptides remains a problem (A. G. Cochran *Chem. Biol.* 2000, 7, R85-R94).

SUMMARY OF THE INVENTION

The invention described below provides peptide templates consisting of residues of naturally occurring L-α-amino acids, whose function is to restrain the peptide loop backbone into a hairpin geometry in a stabilized β-hairpin conformation. These templates can be used for the construction of phage display derived template fixed β-hairpin loop mimetics generating phage display libraries with very high binding constants to targets.

This method provided by the invention can be advantageously used in screening of large libraries of phage display derived template fixed β-hairpin loop mimetics which in turn considerably facilitates structure-activity studies, and hence the discovery of new molecules with potent activities and with novel selectivities towards different types of targets.

Due to the structurally and conformationally well-defined architecture of the β-hairpin loop mimetics of the general formula I, as defined hereinbelow, key amino acid residues or motifs within the chain Z-encoded as nucleic acid sequences in phage display libraries—can be integrated in conformationally locked arrangements. By shifting these key amino acid residues or motifs along the β-hairpin structure, new arrangements of important amino acids can be scanned (positional scanning of key sequences). Alternatively, protein sequences can be mapped in order to detect β-hairpin loop motifs. This technique, in summary, allows determining rapidly key amino acids and motifs (hotspots) important for binding in large surface and flat protein interfaces not only in their sequential but also in their spatial arrangement. This information can ultimately be used for the design of small peptidomimetic drug candidates (Cunningham, B. C.; Wells, J. A. *Curr. Opin. Struct. Biol.* 1997, 7, 457; Obrecht, D.; Altorfer, M.; Robinson, J. A. *Adv. Med. Chem.* Vol. 4, 1-68, JAI Press Inc., 1999).

DETAILED DESCRIPTION OF THE INVENTION

Figure 1:
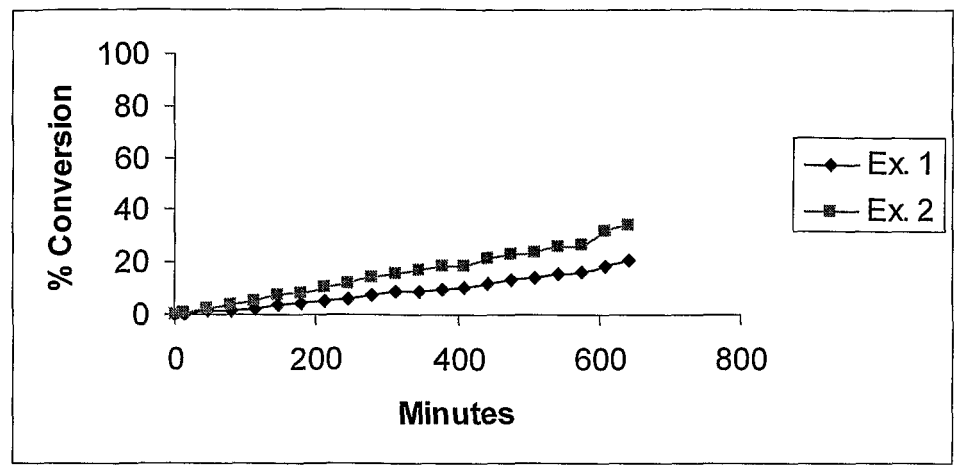
FIGS. 1-6 show a comparison of the formation of disulfide bridged β-hairpin mimetics in % up to a time after which no progress of conversion was detected.

The template fixed β hairpin loop mimetics of the present invention are compounds of the general formula

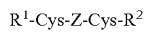

$$R^1\text{-Cys-Z-Cys-}R^2 \qquad \text{I}$$

wherein
the two Cys residues are bridged by a disulfide bond thereby forming a cyclic peptide; $R^1$ and $R^2$ are
A-B and B-C; or B-A and C-B; or C-B and B-A; or B-C and A-B; or C-A and C-A; or A-C and A-C; or C-A and C-B; or B-B and C-B; or B-B and B-C; or A-B and C-C; or B-A and C-C; or C-B and B-B; or B-C and B-B; or C-C and B-A; or C-C and A-B; or B-B and C-C; or C-C and B-C; or A-C and B-C; or C-B and C-A; or B-C and A-C; or A-C and A-B; or B-A and C-A; A-A and C-C; or C-C and A-A; or A-B-C and A-B-C; or B-A-B and B-C-B; or B-C-B and B-A-B; or A-B-B and B-C-C; or C-B-B and B-B-A; or A-C-B and B-A-C; or C-A-B and B-C-A; or B-A-B and B-C-C; or B-C-B and B-A-C; or C-C-B and B-B-A; or C-C-B and B-A-B, or C-B-B and C-C-A; or A-C-C and B-B-C; or B-C-C and B-A-B; or B-C-C and B-A-C; or A-B-B and B-C-C; or B-A-B and C-C-B; or C-A-B and C-C-B; or B-B-B and B-C-C; or C-B-B and B-B-B; or B-B-B and C-C-B; or B-C-C and B-B-B; or A-B-C and B-B-C; or C-B-B and C-B-A; or A-B-C and A-C-C; or C-C-A and C-B-A; or B-A-C and A-C-B; or B-C-A and C-A-B; or C-B-A and C-B-A; or A-A-B and B-C-C; or C-C-B and B-A-A; or B-B-C and A-C-C; or B-B-C and A-B-C; or B-B-C and B-A-C and B-C-C; or C-C-A-B; or C-C-B and C-A-B; or A-B-C and B-C-C; or A-B-C and B-C-C; or C-A-B and B-C-B; or B-C-B and B-B-C; or C-B-B and B-C-B; or B-C-B and B-B-B; or B-B-B and B-C-B; or C-B-B and B-C-A; or A-C-B and B-B-C; or C-B-B and C-B-B; or B-B-B and B-B-B; or B-B-B and B-B-C; or A-A-C and A-C-C; or C-C-A and C-A-A; or A-A-C and A-C-B; or B-C-A and C-A-A; or A-A-C and B-C-C; or C-C-B and C-A-A; or A-A-B and C-C-B; or B-C-C and B-A-A; or A-B-A and C-B-C; or C-B-C and A-B-A; or A-B-B and C-B-C; or C-B-C and B-B-A; or B-A-A and C-C-B; or B-C-C and A-A-B; or B-B-A and C-B-B; or B-B-C and A-C-B; or B-B-C and A-C-B; or B-C-A and C-B-B; or B-C-B and C-B-B; or B-B-C and B-C-B; or B-C-B and C-A-B; or B-A-C and B-C-B; or B-C-B and C-B-B; or B-A-C and A-C-B; or B-A-C and A-C-C; or C-C-A and C-A-B; or B-A-C and B-C-C; B-C-C and A-A-C; or C-A-A and C-C-B; or C-A-A and C-C-A; or A-C-C and A-A-C; or C-B-A and C-C-A; or A-C-C and A-B-C; or C-B-A and C-B-B; or C-B-A and C-C-B; or B-C-C and A-B-C; or C-B-B and C-C-A; or C-B-A and C-B-B; or C-B-B and C-C-B; or B-CC and B-B-C; or C-C-A and C-A-B; or C-C-A and C-C-B; or C-C-B and B-B-B; or C-C-B and C-A-A; or C-C-B and C-B-A; or C-C-B and B-C-B; or B-B-C and B-C-B; or A-C-B and B-B-C; or A-C-C and B-B-C;

A being any one of Asn, Gln, Asp, Glu, Thr, Ser and Gly;

B being any one of Val, Ile, Ser, Thr, Phe, Tyr, Trp and Gly; and

C being any one of Arg, Lys and Gly; and

Z is a chain of n amino acid residues with n being an integer form 4 to 20 and with each of these n amino acid residues being, independently, derived from any naturally occurring L-α-amino acid.

For example, Z contains one of the key sequences -Arg-Gly-Asp-, -Glu-Leu-Arg-, -Arg-Lys-Lys- and -Lys-Gly-Phe- or consists of, or contains one of the key sequences -Val-Arg-Lys-Lys-[SEQ ID NO:1], -Lys-Lys-Tyr-Leu-[SEQ ID NO:2], -Trp-Leu-Asp-Val-[SEQ ID NO:3], -Tyr-Ile-Arg-Leu-Pro-[SEQ ID NO:4], -Tyr-Ile-Gly-Ser-Arg-[SEQ ID NO:5], -Ile-Lys-Val-Ala-Val-[SEQ ID NO:6], -Pro-Pro-Xaa-Xaa-Trp-[SEQ ID NO:7] wherein Xaa can be residues of any naturally occurring L-α-amino acids, -Leu-Trp-Tyr-Ser-Asn-His-Trp-Val-[SEQ ID NO:22], -Lys-Trp-Phe-Ser-Asn-His-Tyr-Gln-[SEQ ID NO:23], -Phe-Leu-Ala-His-Tyr-Ala-[SEQ ID NO:24] and -Leu-Trp-Tyr-Ser-Asn-His-Trp-Val-Lys-Trp-[SEQ ID NO:25]; these key sequences will be discussed in more detail hereinafter.

The library of template-fixed β-hairpin mimetics of the present invention comprises a plurality of compounds of the above general formula I. This library of the template fixed β-hairpin mimetics can be fused to at least a portion of phage coat protein, and the template fixed β-hairpin mimetics are displayed on the surface of a phage or phagemid particle.

The invention also provides a screening method for template fixed hairpin β-mimetics having a template that conformationally stabilizes a β-hairpin conformation and which are capable of binding to a specific binding partner comprises the steps of a) providing a library of template fixed β-hairpin mimetics of formula I which may be fused to at least a portion of phage coat protein where the template-fixed β-hairpin mimetics are displayed on the surface of a phage or phagemid particle;

b) contacting the library of step a) with a binding partner;

c) selecting from the library phage peptides capable of forming a non-covalent complex with the binding partner; and d) optionally isolating the peptides or determining the sequence by DNA-analysis of step c).

In such method the binding partner is normally an antibody, an enzyme, a receptor or a ligand or fragments or portions thereof.

Phage peptides which have been determined and optionally isolated by the above process and synthetic peptides having structures which are identical to the structures of the peptides thus determined and optionally isolated also form part of the present invention.

The structural elements forming the templates consist of the two disulfide-bridged Cys residues together with the residues $R^1$ and $R^2$, which comprise either both two or both three amino acid residues which, as described below, are capable of stabilizing β-sheet conformation and which are positioned on opposite sites of the antiparallel β-strands adjacent to the disulfide bond; furthermore these templates have an N-terminus and a C-terminus oriented to be linked to the chain Z. The peptide chain Z is linked to the C-terminus and the N-terminus of the templates via the corresponding N- and, respectively, C-termini so that the template and the chain combine to a cyclic structure.

As amino acid residues there come into consideration those which are derived from naturally occurring L-α-amino acids. Hereinafter there is given a list of these amino acids which, or the residues of which, are suitable for the purposes of the present invention, the abbreviations corresponding to generally adopted usual practice.

| | | |
|---|---|---|
| Ala | A | L-Alanine |
| Arg | R | L-Arginine |
| Asn | N | L-Asparagine |
| Asp | D | L-Aspartic acid |
| Cys | C | L-Cysteine |
| Glu | E | L-Glutamic acid |
| Gln | Q | L-Glutamine |
| Gly | G | Glycine |
| His | H | L-Histidine |
| Ile | I | L-Isoleucine |
| Leu | L | L-Leucine |
| Lys | K | L-Lysine |
| Met | M | L-Methionine |
| Phe | F | L-Phenylalanine |
| Pro | P | L-Proline |
| Ser | S | L-Serine |
| Thr | T | L-Threonine |
| Trp | W | L-Tryptophan |
| Tyr | Y | L-Tyrosine |
| Val | V | L-Valine |

$R^1$ and $R^2$ comprise either each two or each three amino acid residues which hereinabove have been represented by the Symbols A, B and C, each of which stands for one of the following groups:

Group A: amino acid residues capable of formation of ion bond or hydrogen bond interaction;
Group B: amino acid residues capable of formation of hydrophobic interaction; and
Group C: amino acid residues capable of formation of cationic-π interaction or ion bond or hydrogen bond.

Group A comprises amino acids containing side chains with polar-non-charged or acidic residues. A polar-non-charged residue refers to a hydrophilic side chain that is uncharged at physiological pH. Such side chains typically contain hydrogen bond donor groups such as primary and secondary amides or alcohols. An acidic residue refers to a hydrophilic side chain that contains a carboxylic group. The naturally occurring polar-non-charged or acidic L-α-amino acids are asparagine, glutamine, aspartic acid, glutamic acid, threonine, and serine. Glycine is included in group A as a neutral β-sheet former. The amino acid side chains can form an interstrand ionic bond (salt bridge) or a hydrogen bond interaction with amino acid residues group C at opposite positions of the anti-parallel β-sheet and, in addition, an intrastrand hydrogen or ionic bond interaction with amino acid residues of group C of tripeptide moieties (Clani B. et al., *J. Am. Chem. Soc.* 2003, 125, 9038-9047; Searle, M. S. et al., *J. Am. Chem. Soc.* 1999, 121, 11615-11620) within the template.

Group B comprises amino acid residues containing small to medium sized hydrophobic, or aromatic or heteroaromatic, or polar-non-charged side chain residues. A hydrophobic small- to medium-sized residue refers to an amino acid side chain that is uncharged at physiological pH. An aromatic amino acid residue refers to a hydrophobic amino acid having a side chain containing at least one ring having a conjugated or π-electron system (aromatic group). In addition they may contain hydrogen bond donor groups such as primary and secondary amines and alcohols. A polar-non-charged residue refers to a hydrophilic side chain that is uncharged at physiological pH. Such side chains typically contain hydrogen bond donor groups such as alcohols. The naturally occurring small-to-medium-sized L-α-amino acids, aromatic and heteroaromatic L-α-amino acids and polar-non-charged L-α-amino acids are valine, isoleucine, serine, threonine, phenylalanine, tyrosine, and tryptophane. Glycine is included in group B as a neutral β-sheet former. The amino acid side chains can form an interstrand hydrophobic-hydrophobic interaction with amino acid residues group B or hydrophobic (π)-cationic interaction with amino acid residues group C at opposite positions of the anti parallel β-sheet and, in addition, an intrastrand hydrophobic or hydrophobic-cationic interaction with amino acid residues of group B or C of tripeptide moieties within the template.

Group C comprises amino acids containing side chains with polar-cationic residues. Polar cationic refers to a basic side chain which is protonated at physiological pH. The naturally occurring polar-cationic L-α-amino acids are arginine and lysine (Clani B. et al., *J. Am. Chem. Soc.* 2003, 125, 9038-9047; Searle, M. S. et al., *J. Am. Chem. Soc.* 1999, 121, 11615-11620). Glycine is included in group C as a neutral β-sheet former. The amino acid side chains of arginine and lysine can form an interstrand cationic-hydrophobic (7)-interaction (J. P. Gallivan, D. A. Dougherty, *Proc. Natl. Acad. Sci. USA* 1999, 96, 9459-9464) with amino acid residues type B or ionic bond interaction (salt bridge) or hydrogen bond interaction with group A amino acid residues at opposite positions of the anti parallel β-sheet and, in addition, an intrastrand cationic-hydrophobic (π)-interaction with amino acid residues of group B of tripeptide moieties within the template.

$R^1$ and $R^2$ are preferably

```
Glu-Thr and Thr-Lys; or Lys-Thr and Thr-Glu; or

Thr-Glu and Lys-Thr; or Thr-Lys and Glu-Thr; or

Leu-Glu and Lys-Val; or Val-Lys and Glu-Leu; or

Glu-Leu and Val-Lys; or Lys-Leu and Val-Glu; or

Asn-Gly and Lys-Val; or Val-Gly and Lys-Asn; or

Gly-Asn and Val-Lys; or Gly-Val and Asn-Lys; or

Gly-Gly and Gly-Gly; or

Glu-Leu-Lys and Glu-Val-Lys; or

Lys-Val-Glu and Lys-Leu-Glu; or

Leu-Glu-Lys and Glu-Lys-Val; or

Val-Lys-Glu and Lys-Glu-Leu- or

Glu-Lys-Leu and Val-Glu-Lys; or

Lys-Glu-Val and Leu-Lys-Glu; or

Lys-Glu-Leu and Val-Lys-Glu; or

Glu-Lys-Val and Leu-Glu-Lys; or

Lys-Val-Gly and Gly-Leu-Glu; or

Glu-Leu-Gly and Gly-Val-Lys; or

Val-Lys-Gly and Gly-Glu-Leu; or

Leu-Glu-Gly and Gly-Lys-Val; or

Val-Gly-Lys and Glu-Gly-Leu; or
```

-continued

Leu-Gly-Glu and Lys-Gly-Val; or

Gly-Gly-Gly and Gly-Gly-Gly.

The positions $P^1$ to $P''$ of each amino acid residue in the chain Z is unequivocally defined as follows: $P^1$ represents the first amino acid in the chain Z that is coupled with its N-terminus to the C-terminus of the template and $P''$ represents the last amino acid in the chain Z, that is coupled with its C-terminus to the N-terminus of the template.

Advantageously the chain Z consist of, or contains, a key sequence of two, three, four, five, six or occasionally up to ten amino acid residues, the two terminal members of which are "constant" ("k") whilst any other members are either "constant", too, or "variable" ("x"), in all possible combinations or permutations. The two terminal "constant" members can be the same or different, and the same applies to any remaining "constant" and/or to any "variable" members.

The key sequences can be translated into oligo-nucleic acid sequences and transplanted into phage displayed peptides of the invention.

Particularly suitable "constant" members ("k") are Trp, Arg, Tyr, Ile, Asp, His, Lys, Glu and Thr, further suitable "constant" members ("k") are Gln, Phe, Met and Ser, and suitable "variable" members ("x") are Ala, Leu and Val.

Key sequences of two, three, four, five and six amino acid residues, can be schematically depicted as follows:

dipeptide
-$k^1$-$k^2$-
tripeptide
-$k^1$-$k^2$-$k^3$-
tetrapeptide
-$k^1$-$k^2$-$k^3$-$k^4$-
-$k^1$-$x^1$-$k^2$-$k^3$-
-$k^1$-$k^2$-$x^1$-$k^3$-
-$k^1$-$x^1$-$x^2$-$k^2$-
pentapeptide
-$k^1$-$k^2$-$k^3$-$k^4$-$k^5$-
-$k^1$-$x^1$-$k^2$-$k^3$-$k^4$-
-$k^1$-$k^2$-$x^1$-$k^3$-$k^4$-
-$k^1$-$k^2$-$k^3$-$x^1$-$k^4$-
$k^1$-$x^1$-$x^2$-$k^2$-$k^3$-
-$k^1$-$k^2$-$x^1$-$x^2$-$k^3$-
-$k^1$-$x^1$-$k^2$-$x^2$-$k^3$-
-$k^1$-$x^1$-$x^2$-$x^3$-$k^2$-
hexapeptide
-$k^1$-$k^2$-$k^3$-$k^4$-$k^5$-$k^6$-
-$k^1$-$x^1$-$k^2$-$k^3$-$k^4$-$k^5$-
-$k^1$-$k^2$-$x^1$-$k^3$-$k^4$-$k^5$-
-$k^1$-$k^2$-$k^3$-$x^1$-$k^4$-$k^5$-
-$k^1$-$k^2$-$k^3$-$k^4$-$x^1$-$k^5$-
-$k^1$-$x^1$-$x^2$-$k^2$-$k^3$-$k^4$-
-$k^1$-$k^2$-$x^1$-$x^2$-$k^3$-$k^4$-
-$k^1$-$k^2$-$k^3$-$x^1$-$x^2$-$k^4$-
-$k^1$-$x^1$-$x^2$-$x^2$-$k^3$-$k^4$-
-$k^1$-$k^2$-$x^1$-$k^3$-$x^2$-$k^4$-
-$k^1$-$x^1$-$k^2$-$k^3$-$x^2$-$k^4$-
-$k^1$-$x^1$-$x^2$-$x^3$-$k^2$-$k^3$-
-$k^1$-$k^2$-$x^1$-$x^2$-$x^3$-$k^3$-
-$k^1$-$x^1$-$k^2$-$x^2$-$x^3$-$k^3$-
-$k^1$-$x^1$-$x^2$-$k^2$-$x^3$-$k^3$-
-$k^1$-$x^1$-$x^2$-$x^3$-$x^4$-$k^2$ Certain key sequences are known to occur in important physiologically active peptides, such as

| Sequence | Description |
|---|---|
| R G D | in fibronectin (FN), vitronectin (VN), osteopontin, collagens, thrombospondin, fibrinogen (Fg), von Willebrand factor (vWF), see Obrecht, D.; Altorfer, M.; Robinson, J. A. Adv. Med. Chem. Vol. 4, 1-68, JAI Press Inc., 1999 |
| E L R | in C X C chemokines, see Saunders, J.; Tarby, C. M. Drug Discovery Today, 1999, 4, 80-92 |
| R K K | see J. Biol. Chem. 1999, 274, 3513 |
| K G F | see Prot. Sci. 1998, 7, 1681-1690 |
| V R K K [SEQ ID NO: 1] | in Platelet-Derived Growth Factor (PDGF), see Ross, R.; Raines, E. W.; Bowden-Pope, D. F. Cell, 1986, 46, 155-159 |
| K K Y L [SEQ ID NO: 2] | in VIP (vasointestinal peptide) showing neuroprotective properties against β-amyloid neurotoxicity, see Proc. Natl. Am. Soc. USA 1999, 96, 4143-4148 |
| W L D V [SEQ ID NO: 3] | in integrin $α_4β_1$, see Europ. J. Biol. 1996, 242, 352-362 and Int. J. Pept. Prot. Res. 1996, 47, 427-436 |
| Y I R L P [SEQ ID NO: 4] | in Factor Xa inhibitors, see Al Obeidis, F.; Ostrem, J. A. Drug Discovery Today 1998, 3, 223-231 |
| Y I G S R [SEQ ID NO: 5] | in laminine, see EMBO. J. 1984, 3, 1463 |
| I K V A V [SEQ ID NO: 6] | see Cell 1987, 88, 989 |
| P P R X X W [SEQ ID NO: 7] | see J. Biol. Chem. 1998, 273, 11001-11006 & 11007-11011 |

Phage display is a technique by which variant polypeptides are displayed as fusion proteins to a coat protein on the surface of a phage, filamentous phage particles, as described in "Phage Display of Peptides and Proteins", B. K. Kay, J. Winter, J. Mc Cafferty 1996, Academic Press.

As used in this description, the term "coat protein" means a protein at least a portion of which is present on the surface of the virus particle. The coat protein may be the major coat protein or may be a minor coat protein.

The term "electroporation" means a process in which foreign matter (protein, nucleic acid, etc) is introduced into a cell by applying a voltage to the cell under conditions sufficient to allow uptake of the foreign matter into the cell. The foreign matter is typically DNA.

A "fusion protein" is a polypeptide having two portions covalently linked together, where each of the portions is a polypeptide having a different property.

A "phagemid" is a plasmid vector having a bacterial origin of replication, ColE1, and a copy of an intergenic region of a bacteriophage. The phagemid may be based on any known bacteriophage, including filamentous bacteriophage. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13 phage or a derivative thereof, a lambdoid phage such as, but not limited to, phi80, phages 21, 82, 424, 432, lambda.imm343, lambda.imm21, lambda.EMBL or lamdab.gt., or all derivatives, genetically engineered derivatives, and hybrids thereof.

"Ligation" is a process of forming phosphodiester bonds between two nucleic acid fragments. For ligation of the two fragments, the ends of the DNA fragments need to be compatible with each other. In most cases, the ends will be directly compatible after endonuclease digestion. However, it may be necessary first to convert the staggered ends commonly produced after endonuclease digestion to blunt ends to make them compatible for ligation. For the creation of blunt ends, DNA-modifying enzymes like T4 polymerase or Klenow are used under the conditions as described by the supplier.

DNA purification is performed by phenol-chloroform, gelpurification or kits commercially available on the market.

After endonuclease digestion the DNA may be gel-purified using polyacrylamide or agarose gel electrophoresis before ligation. The DNA can be purified by standard molecular biology techniques (Sambrook et al. M: A Laboratory Manual, Sambrook et al. Molecular Cloning. A Laboratory Manual, Cold Spring Harbor, Laboratory Press, 1989) or applying commercially available kits such as, but not limited to, QIAquick gel extraction kit (Qiagen, Inc., Chatsworth, Calif.).

Prior to the ligation reaction linearized vector fragments may be treated with bacterial alkaline phosphatase or calf intestine alkaline phosphatase to prevent self-ligation during the ligation step. The ligation reaction is preferably catalyzed by T4 DNA ligase. As known to the routine practitioner ligation conditions can vary in time, temperature, concentration of buffers, quantities of DNA molecules to be ligated, and amounts of ligase and ATP.

"Oligonucleotides" are short length, single- or double-stranded polydeoxy nucleotides that are chemically synthesized by known methods. Alternatively, if the target amino acid sequence is known, one may infer potential nucleic acid sequences using known and preferred coding residues for each amino acid residue.

By "binding partner complex" is meant the association of two or more molecules which are bound to each other in a specific, detectable manner, thus the association of ligand and receptor, antibody and antigen.

The synthetic process for obtaining the compounds of the invention can advantageously be carried out as parallel array synthesis to yield libraries of template-fixed β-hairpin mimetics of the above general formula I. Such parallel synthesis allows one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene grafted with polyethyleneglycol spacers (Tentagel$^R$); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 2-methoxy-4-hydroxymethylphenoxy (Sasrin$^R$ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably, 1-5%, divinylbenzene and functionalized by means of the 2-chlorotrityl linker.

When carried out as a parallel array synthesis the process of the invention can be advantageously carried out as described herein below but it will be immediately apparent to those skilled in the art how this procedure will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing at least one component of a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin$^R$ linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Florsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present also in the side-chain of lysine)

| Cbz | benzyloxycarbonyl |
|---|---|
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl (or trityl) | for the carboxyl group (as is present also in the side-chain of aspartic and glutamic acid) by conversion into esters with the alcohol components

| tBu | tert.-butyl |
|---|---|
| Bn | benzyl |
| Me | methyl |
| Ph | phenyl |
| Pac | Phenacyl |
|  | Allyl |
| Tse | trimethylsilylethyl |
| Tce | trichloroethyl | for the guanidino group (as is present in the side-chain of arginine)

| Boc | t-Butyloxycarbonyl |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e.g. in the side-chain of threonine and serine)

| tBu | tert.-butyl |
|---|---|
| Bn | benzyl |
| Trt | trityl | and for the mercapto group (as is present in the side-chain of cysteine)

| Acm | acetamidomethyl |
|---|---|
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2%. DBU/2% piperidine in DMF can be used.

The quantity of the reactant, i.e. of the amino acid derivative, is usually 1 to 20 equivalents based on the mmols per gram (meq/g) loading of the functionalized solid support (typically 0.1 to 2.85 mmol/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are ACT 90, Symphoni abi 433A peptide synthesizer and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, is soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP) (Castro et al., *Tetrahedron Lett.* 1975, 14, 1219-1222; *Synthesis*, 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium terafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent.

2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Before this fully protected linear peptide is detached from the solid support, it is possible, if desired, to selectively deprotect the protected α-amino group of the N-terminal amino amino acid residue and to acylate the amino group thus liberated by means of an acylating agent corresponding to the acyl substituent to be introduced. Alternatively the protecting groups of the cysteines can be first selectively removed and cyclisation can be effected as described below. The cleavage from the resin and the deprotection of the cyclic peptide can be done as described below.

The fully protected peptide derivative is treated with 82.5% TFA, 5% $H_2O$, 5% phenol, 5% thioanisol, 2.5% ethanthiol or another combination of scavengers for effecting the cleavage of protecting groups. The cleavage reaction time is commonly 30 minutes to 12 hours, preferably about 5 hours. Thereafter most of the TFA is evaporated and the product is precipitated with ether or other solvents which are suitable therefor. After careful removal of the solvent, the peptide derivative obtained can be purified.

Cyclization (formation of the disulfide bridge) is then effected in solution using solvents such as water, DMF and the like. Various oxidation reagents can be used for the cyclization, such as $H_2O_2$, air, or iodine. The duration of the cyclization is about 15 minutes to 24 hours, preferably about 40 minutes. The progress of the reaction is followed, e.g. by RP-HPLC (Reverse Phase High Performance Liquid Chromatography) and mass spectrometry. Then the solvent is removed by evaporation, and the cyclic peptide derivative is purified by RP-HPLC.

The phage display process of the invention can be carried out as followed:

The template fixed β-hairpin loop mimetic of the invention is fused to at least a portion of phage coat protein to form a fusion protein containing the template fixed β-hairpin loop mimetic. The fusion protein can be made by expressing a gene fusion encoding the fusion protein using known techniques of phage display such as those described below.

Bacteriophage phage display is a known technique by which variant polypeptides are displayed as fusion proteins to the coat protein on the surface of bacteriophage particles (Scott, J. K. and Smith, G. P. Science 1990, 249; 386). The utility lies in the fact that large libraries of selectively randomized protein variants (or randomly cloned cDNAs) can be rapidly and efficiently sorted for those sequences that bind to a target molecule with high affinity.

Typically, variant polypeptides such as the template fixed β-hairpin mimetic of the invention, are fused to gene III protein which is displayed at one end of the virion.

Monovalent phage display is a process in which a protein or peptide sequence is fused to a portion of a gene III protein and expressed at low levels in the presence of wild type gene III protein so that particles display mostly wild-type gene III protein and one copy or none of the fusion protein which can also be used within the invention.

Suitable gene III vectors for display of template fixed β-hairpin mimetic of the invention include fUSES, MKE 13 (New England Biolabs, Inc), fAFF1 (Cwirla et al, *Proc. Natl. Acad. Sci. USA,* 1990, 87, 6378-6382), fd-CAT1, fdtetDOG, 33,88, pComb3, pComb8,m663, pHEN1, pCANTAB5E genentech vectors CB and the like.

Phage display methods for proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle contacting the recombinant phage particles with a target molecule so that at least a portion of the particle bind to the target, and separating the particles which bind from those that do not bind, are known and maybe used in accordance with the invention (O'Neil K. and Hoess R., *Curr. Opin Struct. Biol.* 1995 5, 443-449).

The gene encoding the coat protein of the phage and the gene encoding the desired template fixed β-hairpin mimetic portion of the fusion protein can be obtained by methods known in the art (Sambrook et al. Molecular Cloning. A Laboratory Manual, Cold Spring Harbor, Laboratory Press, pp. A1-A4 1989). The DNA encoding the gene may be chemically synthesized (Letzinger and Khorona. *J. Am. Chem. Soc.* 1965, 87, 3526, ibd. 1966, 88, 3181; L. J. McBride, M. H. Caruthers, *Tetrahedron Lett.* 1983, 24, 245-248), and then mutated to prepare a library of variants as described below.

To ligate DNA fragments together to form a functional vector containing the fusion gene, the ends of the DNA fragments must be compatible with each other. It may be necessary to first convert the sticky ends commonly produced by endonuclease digestion to blunt ends to make them compatible for ligation. To blunt the ends, the DNA is treated in a suitable buffer for at least 15 minutes at 15° C. of the Klenow fragment of DNA polymerase 1 (Klenow) in the presence of the four deoxynuceotide triphosphates. The DNA is then purified by phenol-chloroform extraction and ethanol precipitation or other DNA purification technique.

The cleaved DNA fragments may be size separated and selected using gel electrophoresis. The DNA may be electrophoresed through either an agarose or a polyacrylamide matrix. After electrophoresis the DNA is extracted from the matrix by electroelution or methods for purification and ligation.

The DNA fragments that are to be ligated together are put in solution in about equimolar amounts. The solution will also contain ATP, ligase buffer and a ligase such as T4 DNA ligase.

After ligation the vector with the foreign gene now inserted is purified by standard molecular biology methods (Sambrook et al. Molecular Cloning. A Laboratory Manual, Cold Spring Harbor, Laboratory Press, 1989) and transformed into a suitable host cell. The preferred method of transformation is electroporation which may be carried out using methods known in the art. For library construction, the DNA is preferably present at a final concentration of 0.05-0.2 microgram per 100 microliter of competent cells suspension.

The DNA is preferably purified to remove contaminants. The DNA may be purified by any known method; however, a preferred purification method is the use of DNA affinity purification. The purification of DNA using DNA binding resins and affinity reagents is well known and any of the methods well known in the art (eg. Biorad, Qiagene) can be used in this invention.

Any suitable cells which can be transformed by electroporation may be used as host cells in the method of the invention. Suitable host cells which can be transformed include gram negative cells such as E. coli. Suitable E. coli strains include, but are not limited to, XL1 Blue (Stratagene), ElectroTen-Blue (Stratagene,), ER2738 (New England Biolabs), DH5α (Gibco), MC1061 (American Type Culture Collection (ATTC), ATTC number 53338).

Cell concentration of about $10^{10}$ colony forming units per ml of suspension of viable living cells and greater are preferably used during electroporation. After electroporation, cells are preferably grown in SOC medium. (for preparation of SOC medium see, for example, Sambrook et al. Molecular Cloning. A Laboratory Manual, Cold Spring Harbor, Laboratory Press, pp. A1-A4 1989).

If the amino acids are located close together in the polypeptide chain, they may be mutated simultaneously using one oligonucleotide that encodes for all of the desired amino acid substitutions. Oligonucleotides can be synthesized which contain ambiguous or unambiguous nucleotides at predefined positions such as encoding the templates of the invention. At the ambiguous positions a mixture of all nucleotides or a selected subset of the nucleotides are included during the synthesis. Codons encoding the complete collection of the amino acids can be realized, for example, by the NNK or NNS codon, where N is A, C, G, or T, and K is G or T and S is G or C.

After selection of the transformed cells, these cells are grown in culture and the vector DNA may then be isolated. Phage or phagemid vector DNA can be isolated, purified and analysed by DNA sequencing using methods known in the art.

The present invention demonstrates the advantage of a novel system for rationally designing and analyzing peptides of well-defined structural features. The combinatorial libraries comprising such template fixed β-hairpin mimetics and methods of using thereof provide useful information and tools for exploring protein-protein interaction. The template fixed β-hairpin mimetics disclosed herein or generated according to the disclosure of the invention can be candidates for various biological or therapeutic agents, including but not limited to enzyme inhibitors, ligand antagonists or ligand agonists.

The following Examples illustrate the invention in more detail but are not intended to limit its scope in any way. The following abbreviations are used in these Examples:
HBTU: 1-benzotriazol-1-yl-tetramethylurounium hexafluorophosphate (Knorr et al. *Tetrahedron Lett.* 1989, 30, 1927-1930)
HOBt: 1-hydroxybenzotriazole
DIEA: diisopropylethylamine

EXAMPLES

1. Peptide Synthesis of Template Constrained β-Hairpin Mimetics a) Synthesis
Coupling of the First Protected Amino Acid Residue
0.5 g of 2-chlorotritylchloride resin (Barbs et al. *Tetrahedron Lett.* 1989, 30, 3943-3946) (0.83 mmol/g, 0.415 mmol) was filled into a dried flask. The resin was suspended in $CH_2Cl_2$ (2.5 ml) and allowed to swell at room temperature under constant stirring for 30 min. The resin was treated with 0.415 mMol (1 eq) of the first suitably protected amino acid residue (see below) and 284 µl (4 eq) of diisopropylethylamine (DIEA) in $CH_2Cl_2$ (2.5 ml), and the mixture was shaken at 25° C. for 4 hours. The resin colour changed to purple and the solution remained yellowish. The resin was shaken (30 ml of $CH_2Cl_2$/MeOH/DIEA 17/2/1) for 30 min, then washed in the following order with $CH_2Cl_2$ (1×), DMF (1×), $CH_2Cl_2$(1×), MeOH (1×), $CH_2Cl_2$(1×), MeOH (1×), $CH_2Cl_2$ (2×), $Et_2O$ (2×) and dried under vacuum for 6 hours.

Loading was typically 0.45-0.5 mMol/g.

The following preloaded resins were prepared: Fmoc-Cys(Trt)-chlorotritylresin, Fmoc-Glu(OtBu)-chlorotritylresin, Fmoc-Lys(Boc)-chlorotritylresin, Fmoc-Val-chlorotritylresin and Fmoc-Gly-chlorotritylresin.

Procedure 1
The synthesis was carried out using a Syro-peptide synthesizer (Multisyntech) using 24 to 96 reaction vessels. In each vessel was placed 60 mg (weight of the resin before loading) of the above resin. The following reaction cycles were programmed and carried out:

| Step | Reagent | Time |
| --- | --- | --- |
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |
| 5 | 5 equiv. Fmoc amino acid/DMF + 5 eq. HBTU + 5 eq. HOBt + 5 eq. DIEA | 1 × 120 min |
| 6 | DMF, wash | 4 × 2 min. |
| 7 | $CH_2Cl_2$, wash (at the end of the synthesis) | 3 × 2 min |

Steps 3 to 6 are repeated to add each amino-acid.
Acetylation of the Amino Terminal Amino Acid
Steps 1-4 of procedure 1 were carried out in order to remove the Fmoc protecting group from the N-terminus of the synthesized sequence.

The resins loaded with the peptides were then transferred into 15 ml syringes equipped with a frit and a stopcock. The resins were swelled during 30 minutes with 5 ml of $CH_2Cl_2$. DIEA (0.4 ml) and acetic anhydride (0.1 ml) were added to each reactor. The resins were shaken during 6 hours to one night. The resins were filtered and washed with successively CH$_2$Cl$_2$/MeOH/CH$_2$Cl$_2$/MeOH/CH$_2$Cl$_2$/diethylether. The resins were dried under vacuum.

Cleavage and Deprotection of the Fully Protected Peptide Fragment

After completion of the synthesis, the resin was suspended in 1 ml of 1% TFA in CH$_2$Cl$_2$ (v/v) and 1 ml of 20% DIEA in CH$_2$Cl$_2$ for 3 minutes. This procedure was repeated three times to ensure completion of the cleavage. The filtrate was evaporated to dryness and the product was fully deprotected with the cleavage mixture containing 82.5% trifluoroacetic acid (TFA), 5% water, 5% phenol, 5% thioanisole, and 2.5% ethanedithiol for 5 h at room temperature and then concentrated under vacuum. The peptides were precipitated by adding 10 ml of diethylether, then centrifugated, and the ether phase was removed. The operation was repeated twice with 5 ml of diethylether.

The crude peptides were dissolved in 1 ml of 10% CH$_3$CN in water and 0.5 to 1 ml of DMF, filtered on celite and purified by preparative reverse phase HPLC.

Cyclisation of the Linear Deprotected Peptide

The linear peptides obtained were dissolved in 1.5 ml of water at a concentration of $10^{-4}$ M and 15 µl of H$_2$O$_2$ (0.01M, 1 eq.) were added. The cyclisation time was up to 700 min.

The obtained cyclic peptides were analysed by analytical HPLC and ESI-MS. The analytical data comprising HPLC retention times and ESI-MS are indicated in the examples.

Analytical HPLC retention times (RT, in minutes) were determined using a VYDAC 218MS5215 column of size 0.21 cm×15 cm, 5 µm packing side (silica) with the following solvents A (H$_2$O+0.02% TFA) and B (CH$_3$CN) and the following gradient: 0 min: 92% A, 8% B; 8 min: 62% A 38% B; 9-12 min: 0% A, 100% B, flow: 0.4 ml/min.

Example 1 (n=8) is shown in table 1. The peptide was synthesized starting with the amino acid Cys which was grafted to the resin. Starting resin was Fmoc-Cys(Trt)-chlorotritylresin which was prepared as described above. The linear peptide was synthesized on solid support according to procedure 1 in the following sequence: Resin-Cys-P8-P7-P6-P5-P4-P3-P2-P1-Cys, and it was then acylated, cleaved, deprotected, purified and cyclized, as indicated. HPLC-retention time (minutes) and mass were determined using the gradient described above: RT=7.26 min, [M+H]$^+$=1281.3.

Example 2 (n=8) is shown in table 1. The peptide was synthesized starting with the amino acid Lys which was grafted to the resin. Starting resin was Fmoc-Lys(Boc)-chlorotritylresin which was prepared as described above. The linear peptide was synthesized on solid support according to procedure 1 in the following sequence: Resin-R$^2$-Cys-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=6.41 min, [M+H]$^+$=871.4.

Example 3 (n=10) is shown in table 2. The peptide was synthesized starting with the amino acid Cys which was grafted to the resin. Starting resin was Fmoc-Cys(Trt)-chlorotritylresin which was prepared as described above. The linear peptide was synthesized on solid support according to procedure 1 in the following sequence: Resin-Cys-P10-P9-P8-P7-P6-P5-P4-P3-P2-P1-Cys, and it was then acylated, cleaved, deprotected, purified and cyclized, as indicated. HPLC-retention time (minutes) and mass were determined using the gradient described above: RT=5.74 min, [M+H]$^+$=779.2

Example 4 (n=10) is shown in table 2. The peptide was synthesized starting with the amino acid Lys which was grafted to the resin. Starting resin was Fmoc-Lys(Boc)-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=5.13 min, [M+H]$^+$=1009.2.

Example 5 (n=10) is shown in table 2. The peptide was synthesized starting with the amino acid Cys which was grafted to the resin. Starting resins was Fmoc-Cys(Trt)-chlorotritylresin which was prepared as described above. The linear peptide was synthesized on solid support according to procedure 1 in the following sequence: Resin-Cys-P10-P9-P8-P7-P6-P5-P4-P3-P2-P1-Cys, and it was then acylated, cleaved, deprotected, purified and cyclized, as indicated. HPLC-retention time (minutes) and mass were determined using the gradient described above: RT=6.81 min, [M+H]$^+$=1482.6.

Examples 6 and 7 (n=10) are shown in table 2. The peptides were synthesized starting with the amino acid Val which was grafted to the resin. Starting resin was Fmoc-Val-chlorotritylresin which was prepared as described above. The linear peptides were synthesized on solid support according to procedure 1 in the following sequence: Resin-R$^2$-Cys-P10-P9-P8-P7-P6-P5-P4-P3-P2-P1-Cys-R$^1$, and they were then acylated, cleaved, deprotected, purified and cyclized, as indicated. HPLC-retention time (minutes) and mass were determined using the gradient described above: Example 6: RT=7.24 min, [M+H]$^+$=−977.0; Example 7: RT=6.24 min, [M+H]$^+$=941.2.

Example 8 (n=10) is shown in table 2. The peptide was synthesized starting with the amino acid Gly which was grafted to the resin. Starting resin was Fmoc-Gly-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=6.39 min, [M+H]$^+$=856.0.

Example 9 (n=10) is shown in table 2. The peptide was synthesized starting with the amino acid Lys which was grafted to the resin. Starting resin was Fmoc-Lys(Boc)-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=6.18 min, [M+H]$^+$=972.3.

Example 10 (n=10) is shown in table 3. The peptide was synthesized starting with the amino acid Lys which was grafted to the resin. Starting resin was Fmoc-Lys(Boc)-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=5.49 min, [M+H]$^+$=1142.0.

Example 11 (n=10) is shown in table 3. The peptide was synthesized starting with the amino acid Glu which was grafted to the resin. Starting resin was Fmoc-Glu(Boc)-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=6.85 min, [M+H]$^+$=1033.8.

Example 12 (n=10) is shown in table 3. The peptide was synthesized starting with the amino acid Gly which was grafted to the resin. Starting resin was Fmoc-Gly-chlorotritylresin which was prepared as described above. The linear peptide was synthesized on solid support according to procedure 1 in the following sequence: Resin-R$^2$-Cys-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=6.41 min, [M+H]$^+$=913.0.

Example 13 (n=12) is shown in table 4. The peptide was synthesized starting with the amino acid Cys which was grafted to the resin. Starting resin was Fmoc-Cys(Trt)-chlorotritylresin which was prepared as described above. The linear peptide was synthesized on solid support according to procedure 1 in the following sequence: Resin-Cys-P12-P11-P10-P9-P8-P7-P6-P5-P4-P3-P2-P1-Cys, and it was then acylated, cleaved, deprotected, purified and cyclized, as indicated. HPLC-retention time (minutes) and mass were determined using the gradient described above: RT=5.74 min, [M+H]$^+$=836.5.

Example 14 (n=12) is shown in table 4. The peptide was synthesized starting with the amino acid Lys which was grafted to the resin. Starting resin was Fmoc-Lys(Boc)-chlorotritylresin which was prepared as described above. The linear peptide was synthesized on solid support according to procedure 1 in the following sequence: Resin-R$^2$-Cys-P12-P11-P10-P9-P8-P7-P6-P5-P4-P3-P2-P1-Cys-R$^1$, and it was then acylated, cleaved, deprotected, purified and cyclized, as indicated. HPLC-retention time (minutes) and mass were determined using the gradient described above: RT=5.01 min, [M+H]$^+$=~1065.1.

2a. Method of Measuring the Kinetics of Disulfide Bridge Formation of Template-Fixed β-Hairpin Mimetics Stock solutions of each linear deprotected, purified peptide were prepared, containing 1.5 ml of the peptide solution at a concentration of 10$^{-4}$ M in water. The formation of the disulfide bridge was monitored on analytical LC-MS as described above. The first data point is performed without the oxidation reagent H$_2$O$_2$ at time t 0. The second data point is performed 15 minutes after adding the oxidation reagent H$_2$O$_2$ (15 μl, 0.01M, 1 eq.). Data points were recorded every 33 minutes up to a time after which no progress of conversion was detected.

The amount of disulfide bridged cyclic peptide was calculated based on peak area percentage (manually integrated) of the cyclic peptide at time t minus peak area percentage of the cyclic peptide (manually integrated) at time t0 at a wave length of 220 nm.

2b. Method of Measuring Circular Dichroism

Circular dichroism measurements are sensitive to the secondary structure of both peptides and proteins and have been extensively used to examine the conformation of both (M. Jourdan, S. R. Griffiths-Jones, M. S. Searle, *Eur. J. Biochem.* 2000, 267, 3539-3548; J. T. Pelto, L. R. Mc. Lean, *Analytical Biochemistry,* 2000, 277, 167-176).

Circular Dichroism spectra were obtained on a Jasco J-715 spectropolarimeter, equipped with a spectra manager for windows 95/NT. Version 1.52.01 [Build2]. All measurements were performed at room temperature in quartz cells of 0.1 cm path length in water. Spectra were recorded with a 1 nm bandwidth, five scans were collected to improve the signal-to-noise ratio and the solvent baseline was recorded and subtracted from the spectra of the samples. All CD spectra were smoothed (with the same value), and are reported as molecular ellipticity units (Mol. Ellip.) of peptide residue.

Measurement parameters: Band width: 1.0 nm, response: 1 s, sensitivity: standard, measurement range: 240-190 nm, data pitch: 0.5 nm, scanning speed: 50 nm/min. Concentration of the linear deprotected, purified peptide solutions: 10$^{-4}$ M in water as TFA salts. The pH and purity of the linear deprotected, purified peptides as precursors of the following examples were: Example 3: pH 6.38, purity 91%; Example 4: pH 6.77, purity 89%; Example 5: pH 6.01, purity 98%; Example 9: pH 6.00, purity 94%.

2c. Results:

FIGS. 1-6 show a comparison of the formation of disulfide bridged β-hairpin mimetics in % up to a time after which no progress of conversion was detected.

FIG. 1: Examples 1 and 2 (n=8); disulfide bridge formation rate of the compound of Example 2 having a template is compared to Example 1 as a reference not having a template.

Figure 2:
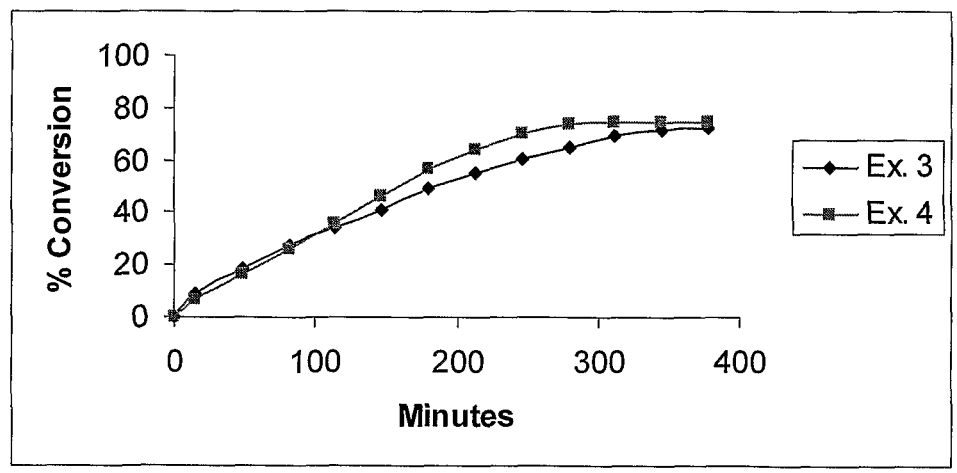

FIG. 2: Examples 3 and 4 (n=10); disulfide bridge formation rate of the compound of Example 4 having a template is compared to Example 3 as a reference not having a template.

Figure 3:
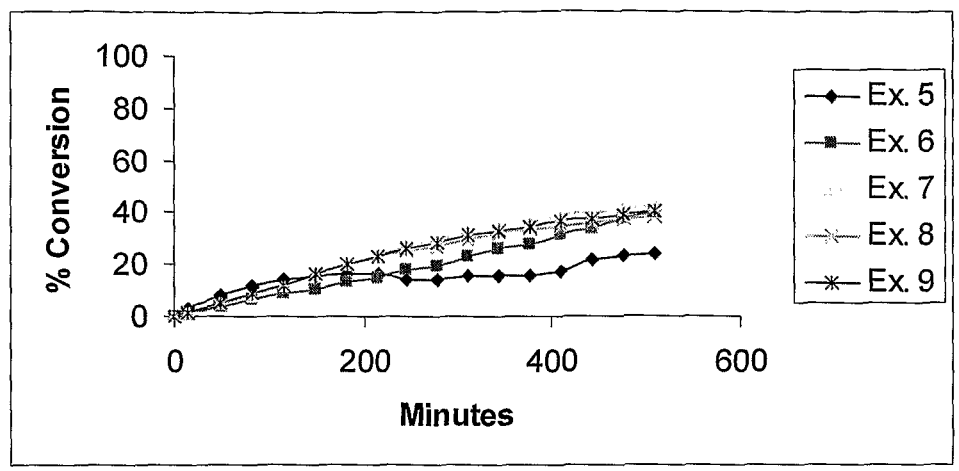

FIG. 3: Examples 5-9 (n=10); disulfide bridge formation rates of the compounds of Examples 6-9 having a template are compared to Example 5 as a reference not having a template.

Figure 4:
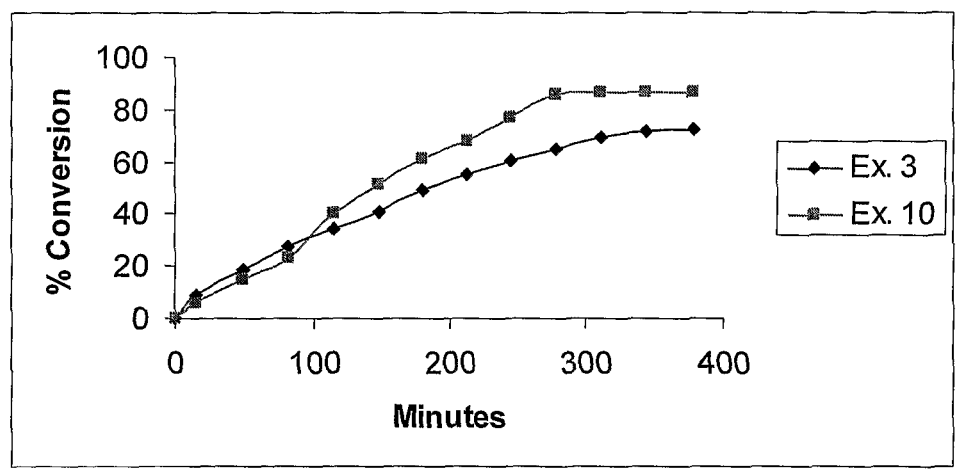

FIG. 4: Examples 3 and 10 (n=10); disulfide bridge formation rate of the compound of Example 10 having a template is compared to Example 3 as a reference not having a template.

Figure 5:
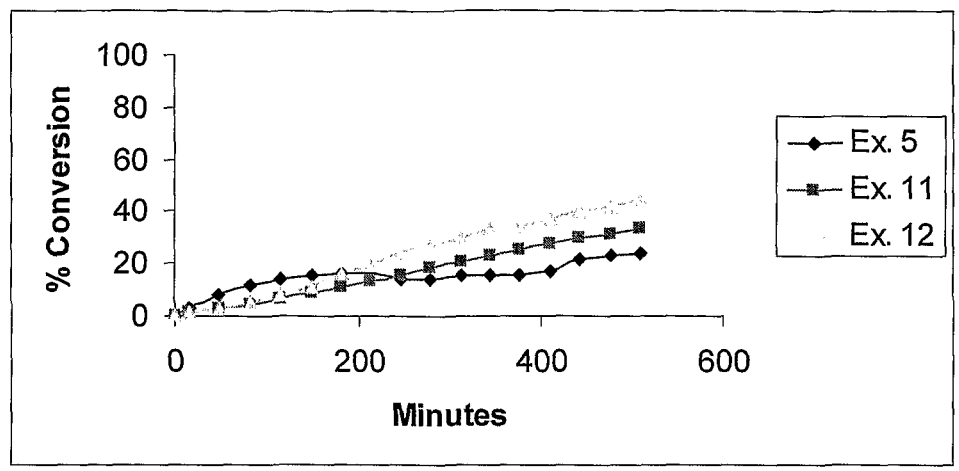

FIG. 5: Examples 5, 11 and 12 (n=10); disulfide bridge formation rates of the compounds of Examples 11 and 12 having a template are compared to Example 5 as a reference not having a template.

Figure 6:
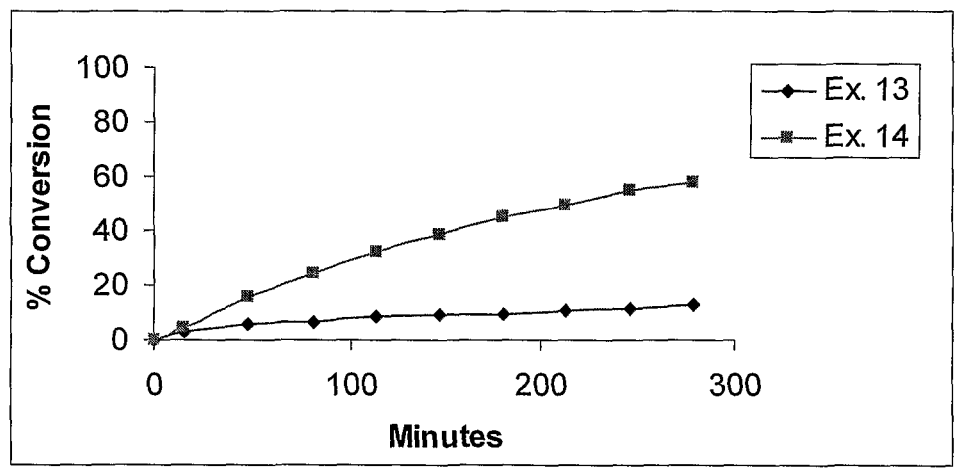

FIG. 6: Example 13 and 14 (n=12); disulfide bridge formation rate of the compound of Example 14 having a template is compared to Example 13 as a reference not having a template.

Figure 7:
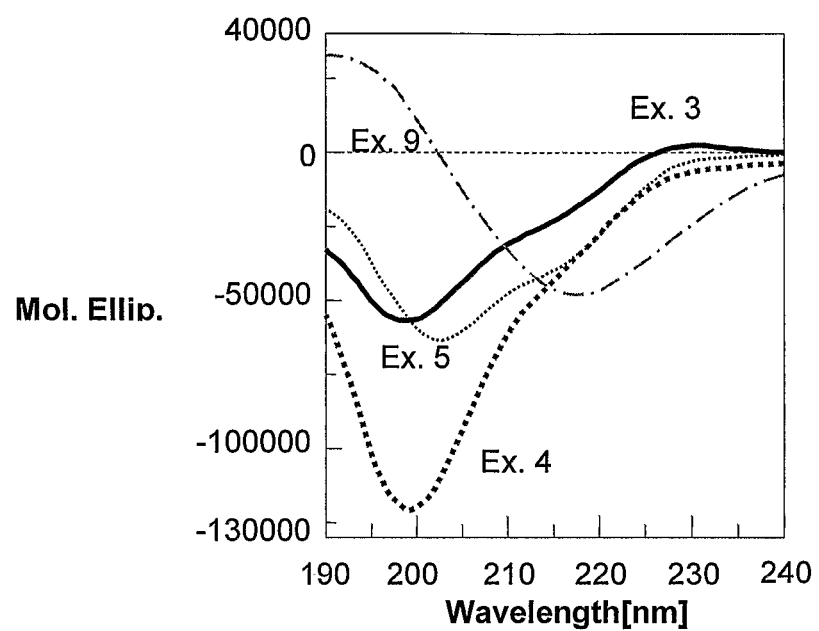
FIG. 7 shows a CD spectra (ε in degxcm²/mol) of the linear peptide precursors of the compounds of Examples 3, 4, 5 and 9, i.e. before disulfide bridge formation.

FIG. 7: CD spectra (ε in degxcm$^2$/mol) of the linear peptide precursors of the compounds of Examples 3, 4, 5 and 9, i.e. before disulfide bridge formation.

2d. Discussion

Design of the Example Sequences Z

Two different types of core peptide sequences Z have been chosen in order to investigate whether the template is facilitating the formation and stabilization of template fixed β-hairpin mimetics: The sequence -Leu-Trp-Tyr-Ser-Asn-His-Trp-Val-[SEQ ID NO:22] was taken from the CDR L3 loop of an antibody (L. Jiang, K. Moehle, J. Robinson, *Chimia* (2000) 54, 558-563) and was modified to the sequence -Lys-Trp-Phe-Ser-Asn-His-Tyr-Gln-[SEQ ID NO:23] containing a stabilizing β-turn and a β-sheet sequence according to P. Y. Chou G. D Fasman, *J. Mol. Biol.* (1977) 115, 135-175 as a reference β-hairpin. A second sequence Z-Phe-Leu-Ala-His-Tyr-Ala-

[SEQ ID NO:24] was constructed from the sequence -Leu-Trp-Tyr-Ser-Asn-His-Trp-Val-Lys-Trp-[SEQ ID NO:25] which does not contain a dedicated stabilizing β-turn sequence or β-sheet sequence according to P. Y. Chou G. D Fasman, *J. Mol. Biol.* (1977) 115, 135-175.

The results depicted in FIGS. 1-6 demonstrate that the disulfide bridge formation rates of compounds with a template and the core sequence -Phe-Leu-Ala-His-Tyr-Ala-[SEQ ID NO:24] is faster compared to those of compounds containing the same core sequence but no template. The results demonstrate clearly that the templates of the invention facilitate the formation of a β-hairpin mimetic effectively. Even in the case of the core sequence Z-Lys-Trp-Phe-Ser-Asn-His-Tyr-Gln-[SEQ ID NO:23] which is itself already containing a stabilizing β-turn and a β-sheet sequence, it can be demonstrated (see FIGS. 2 and 4) that the template facilitates the formation of a β-hairpin mimetic.

In addition the CD-spectrum (see FIG. 7) of the linear precursor of the compound of Example 5 which is containing the core sequence -Phe-Leu-Ala-His-Tyr-Ala-[SEQ ID NO:24] but no template indicates a high content of coil- and α-helix structure and traces of a β-sheet structure, whereas the linear precursor of the compound of Example 9 (containing the same core sequence and a template) indicates a high content of β-sheet structure and a β-turn structure. The CD-spectrum of the linear precursor of the compound of Example 3 containing the core sequence Lys-Trp-Phe-Ser-Asn-His-Tyr-Gln-[SEQ ID NO:23] but no template indicates a mixture of a coil structure and a β-sheet structure whereas the CD spectrum of the linear precursor of the compound of Example 4 (containing the same core structure and a template) indicates a high content of a β-sheet structure. These findings indicate that the templates of the invention induce the formation of a β-hairpin mimetic.

3. Construction of Phage Displayed Template Fixed β-Hairpin Mimetic Sequences Incorporating the Templates Procedure 1:

The oligonucleotide libraries of the invention can be fused to the gene III of the filamentous bacteriophage M13KE according to the procedure of the Ph. D. Peptide Display Cloning System, technical Bulletin # E8101 (Aug. 21, 2002, New England Biolabs, Inc) and K. Noren, C. Noren, *Methods*, 2001, 23, 169-178.

Phage display of the template fixed hairpin mimetic of Example 3 [SEQ ID NO: 10] is accomplished as described in the following section. For all other sequences listed in tables 5-9 corresponding procedures are used, differing in oligonucleotides used to generate insert DNA.

Oligonucleotides 1 and 2 (see below) are used to construct insert DNA. Positions of the unique AccI and EagI restriction sites for cloning into vector DNA are underlined.

For annealing 2 μg (approx. 170 pmol) of oligonucleotide 1 and 4.5 μg of oligonucleotide 2 (approx. 170 μmol) are heated to approximately 95° C. in 50 μl TE (10 mM Tris-HCL, pH 8.0, 1 mM EDTA) containing 100 mM NaCl. After slowly cooling down over 15-30 minutes the annealed duplex is extended with the Klenow fragment of DNA Polymerase I in a total volume of 200 μl. Reaction conditions are as outlined in Sambrook et al. Molecular Cloning. A Laboratory Manual, Cold Spring Harbor, Laboratory Press. The resulting insert DNA was digested with EagI and Acc65I using conditions recommended by the supplier (New England Biolabs). The mixture is extracted with phenol/chloroform and chloroform before precipitation of the aqueous phase with ethanol. The precipitate is purified on an 8% nondenaturing polyacrylamide gel using standard molecular biology procedures (Sambrook et al. Molecular Cloning. A Laboratory Manual, Cold Spring Harbor, Laboratory Press).

15 μg of M13KE vector (New England Biolabs) are digested with EagI and Acc65I according to the conditions recommended by New England Biolabs. The mixture is purified on agarose and linearized vector DNA is recovered with the QIAquick gel extraction kit (Qiagen).

```
oligonucleotide number 1
                                           [SEQ ID NO: 26]
       Acc65I
5' CATGCCCGGGTACCTTTCTATTCTCACTCTGAAACCTGC 3' oligonucleotide number 2
                                           [SEQ ID NO: 27]
       EagI
5' CATGTTTCGGCCGAGCCACCACCTTTGGTGCAGGTCTGATAATGGT

TGCTGAACCATTTGGTGCAGGTTTCAGAGTGAGAATAG' 3'
```

For cloning of insert DNA ligation conditions are unoptimised.

Briefly, ligation is performed overnight at 16° C. in a total volume of 20 μl T4 DNA ligase buffer containing approximately 40 ng linearized vector, approximately 3:1 molar excess of duplex and 200 units of T4 ligase. Control reactions containing vector only, plus and minus ligase, are also performed to determine ligation efficiencies and background due to vector religation. The ligation mixtures are heat-inactivated at 65° C. for 15 minutes and 1 μl aliquots are used for subsequent electroporation into 100 μl ElectroTen-blue electroporation competent cells (Stratagene) as outlined by New England Biolabs. Immediately after electroporation 1 ml SOC medium (2% Bacto tryptone, 0.5% Bacto yeast extract, 10 mM NaCl, 2.5 mM KCl, 10 mM $MgCl_2$, 10 mM $MgSO_4$, 20 mM glucose) is added to each cuvette, and incubations are performed for 30 minutes at 37° C. Aliquots thereof are used for titering each culture by blue/white selection using medium containing X-gal and IPTG. Individual clones for sequence confirmation are selected and incubated in 1 ml of 1:100 dilutions of an overnight culture of XL1-Blue after incubation at 37° C. for 4-4.5 hours. Phage for long-term storage and sequencing purpose are obtained from these liquid cultures applying protocols well known in the art.

Procedure 2: (Randomized Template Fixed β-Hairpin Mimetic Libraries)

Phage display of the sequence of Example 15 [SEQ ID NO 42], see table 9, is representative for the preparation of randomized template fixed β-hairpin mimetic libraries and is described in the following section.

Oligonucleotides 1 and 3 (see above and, respectively, below) are used to construct insert DNA. Positions of the unique AccI and EagI restriction sites for cloning into vector DNA are underlined.

For annealing 2 μg (approx. 170 pmol) of oligonucleotide 1 and 4.5 μg of oligonucleotide 2 (approx. 170 pmol) are heated to approximately 95° C. in 50 μl TE (10 mM Tris-HCl, pH 8.0, 1 mM EDTA) containing 100 mM NaCl. After slowly cooling down over 15-30 minutes the annealed duplex is extended with the Klenow fragment of DNA Polymerase I in a total volume of 200 μl. applying reaction conditions well known in the art (Sambrook et al. Molecular Cloning. A Laboratory Manual, Cold Spring Harbor, Laboratory Press).

The resulting insert DNA is digested with EagI and Acc65I using conditions recommended by the New England Biolabs. The mixture is extracted with phenol/chloroform and chloroform before precipitation of the aqueous phase with ethanol. The precipitate is purified on an 8% non-denaturing polyacrylamide gel using standard molecular biology procedures (Sambrook et al. Molecular Cloning. A Laboratory Manual, Cold Spring Harbor, Laboratory Press).

15 µg of M13KE vector New England Biolabs are digested with EagI and Acc65I according to the conditions recommended by the New England Biolabs. The mixture is purified on agarose and linearized vector DNA is recovered with the QIAquick gel extraction kit (Qiagen).

```
oligonucleotide number 1
                                              [SEQ ID NO: 26]
        Acc65I
5' CATGCCCGGGTACCTTTCTATTCTCACTCTGAAACCTGC 3' oligonucleotide number 3
                                              [SEQ ID NO: 44]
       EagI
5' CATGTTTCGGCCGAGCCACCACCTTTGGTGCAMNNMNNMNNMNNGT

CACCACGMNNMNNMNNGCAGGTTTCAGAGTGAGAATAG 3'
```

Optimal ligation conditions are determined in a total volume of 20 µl varying the molar ratio of insert:vector from 3:1, 5:1 to 10:1 and using 40 and 100 ng of digested vector, respectively. Control reactions containing just vector, in the presence and absence of ligase, are also performed to determine ligation efficiencies and background due to vector religation. Reactions are carried out overnight at 16° C. in 1× ligation buffer and 200 NEB units (=3 Weiss units) of T4 DNA ligase. Test ligations are heat-inactivated at 65° C. for 15 minutes. Subsequent electroporations of 1 µl aliqouts into 100 µl ElectroTen-blue electroporation competent cells (Stratagene) are performed according to recommendations outlined by the manufacturer. Immediately after electroporation 1 ml SOC medium (2% Bacto tryptone, 0.5% Bacto yeast extract, 10 mM NaCl, 2.5 mM KCl, 10 mM $MgCl_2$, 10 mM $MgSO_4$, 20 mM glucose) are added to each cuvette. and incubations are performed for 30 minutes at 37° C. Titers for plaque forming units of each outgrowth culture are determined by blue/white selection with X-gal following standard molecular biology procedures (Sambrook et al. Molecular Cloning. A Laboratory Manual, Cold Spring Harbor, Laboratory Press).

Ligations displaying highest plaque/microgram input vector ratio are scaled up to obtain the desired library complexity. For library construction, the DNA is present at a final concentration of approximately 0.1 microgram per 100 microliter of competent cells suspension. Immediately after electroporation 1 ml SOC medium is added to each cuvette and the SOC outgrowths are grouped in pools of 5 and incubated for 30 minutes at 37° C. The library complexity is determined by titering several outgrowths and the remainders are used for phage amplification. For amplification each pool of SOC outgrowths is added to 1 liter of a 1:100 dilution of an overnight culture of XL1-Blue. Incubation is performed for 4.5-5 hours at 37° C. with vigorous aeration. Phage from these liquid cultures is obtained by clearing the supernatant twice by centrifugation, and precipitating phage particles with polyethylene glycol (final concentration 3.3% polyethylene glycol-8000, 0.4 M NaCl) overnight at 4° C. After centrifugation the obtained pellet is redissolved in TBS, the suspension cleared by centrifugation and phage particles are obtained from the supernatant by precipitation with polyethylene glycol (as described above) for 1 hour at 4° C. The phage pellet after centrifugation is resuspended in TBS (50 mM Tris-HCl, pH 7.5, 100 mM NaCl) and stored at 4° C.

TABLE 1

Examples 1-2, n = 8

| Example | Sequ. ID | $R^1$ | Cys | P1 | P2 | P3 | P4 | P5 | P6 | P7 | P8 | Cys | $R^2$ |
|---|---|---|---|---|---|---|---|---|---|---|---|---|---|
| 1 | SEQ ID NO: 8 | Ac-NH- | Cys | Lys | Trp | Phe | Leu | Ala | His | Tyr | Ala | Cys-H | |
| 2 | SEQ ID NO: 9 | Ac-NH-Glu | Thr | Cys | Lys | Trp | Phe | Leu | Ala | His | Tyr | Ala | Cys | Thr Lys-H | cysteines are linked by a disulfide bridge

TABLE 2

Examples 3-9, n = 10

| Example | Sequ. ID | $R^1$ | | Cys | P1 | P2 | P3 | P4 | P5 | P6 | P7 | P8 | P9 | P10 | Cys | $R^2$ |
|---|---|---|---|---|---|---|---|---|---|---|---|---|---|---|---|---|
| 3 | SEQ ID NO: 10 | Ac-NH- | | Cys | Thr | Lys | Trp | Phe | Ser | Asn | His | Tyr | Gln | Thr | Cys-H | |
| 4 | SEQ ID NO: 11 | Ac-NH-Glu | Thr | Cys | Thr | Lys | Trp | Phe | Ser | Asn | His | Tyr | Gln | Thr | Cys | Thr Lys-H |
| 5 | SEQ ID NO: 12 | Ac-NH- | | Cys | Thr | Lys | Trp | Phe | Leu | Ala | His | Tyr | Ala | Thr | Cys-H | |
| 6 | SEQ ID NO: 13 | Ac-NH-Leu | Glu | Cys | Thr | Lys | Trp | Phe | Leu | Ala | His | Tyr | Ala | Thr | Cys | Lys Val-H |
| 7 | SEQ ID NO: 14 | Ac-NH-Asn | Gly | Cys | Thr | Lys | Trp | Phe | Leu | Ala | His | Tyr | Ala | Thr | Cys | Lys Val-H |

TABLE 2-continued

Examples 3-9, n = 10

| Example | Sequ. ID | R¹ | Cys | P1 | P2 | P3 | P4 | P5 | P6 | P7 | P8 | P9 | P10 | Cys | R² |
|---|---|---|---|---|---|---|---|---|---|---|---|---|---|---|---|
| 8 | SEQ ID NO: 15 | Ac-NH-Gly | Cys | Thr | Lys | Trp | Phe | Leu | Ala | His | Tyr | Ala | Thr | Cys | Gly Gly-H |
| 9 | SEQ ID NO: 16 | Ac-NH-Thr Glu | Cys | Thr | Lys | Trp | Phe | Leu | Ala | His | Tyr | Ala | Thr | Cys | Thr Lys-H | cysteines are linked by a disulfide bridge
Ac = Acetyl

TABLE 3

Examples 10-12, n = 10

| Example | Sequ. ID | R¹ | Cys | P1 | P2 | P3 | P4 | P5 | P6 | P7 | P8 | P9 | P10 | Cys | R² |
|---|---|---|---|---|---|---|---|---|---|---|---|---|---|---|---|
| 10 | SEQ ID NO: 17 | Ac-NH-Glu Leu Lys | Cys | Thr | Lys | Trp | Phe | Ser | Asn | His | Tyr | Gln | Thr | Cys | Glu Val Lys-H |
| 11 | SEQ ID NO 18 | Ac-NH-Lys Val Gly | Cys | Thr | Lys | Trp | Phe | Leu | Ala | His | Tyr | Ala | Thr | Cys | Gly Leu Glu-H |
| 12 | SEQ ID NO: 19 | Ac-NH-Gly Gly Gly | Cys | Thr | Lys | Trp | Phe | Leu | Ala | His | Tyr | Ala | Thr | Cys | Gly Gly Gly-H | cysteines are linked by a disulfide bridge

TABLE 4

Examples 13-14, n = 12

| Example | Sequ. ID | R¹ | Cys | P1 | P2 | P3 | P4 | P5 | P6 | P7 | P8 | P9 | P10 | P11 | P12 | Cys | R² |
|---|---|---|---|---|---|---|---|---|---|---|---|---|---|---|---|---|---|
| 13 | SEQ ID NO: 20 | Ac-NH- | Cys | Gly | Thr | Lys | Trp | Phe | Ser | Asn | His | Tyr | Gln | Thr | Gly | Cys | -H |
| 14 | SEQ ID NO: 21 | Ac-NH-Glu Thr | Cys | Gly | Thr | Lys | Trp | Phe | Ser | Asn | His | Tyr | Gln | Thr | Gly | Cys | Thr Lys-H | cysteines are linked by a disulfide bridge
Ac = Acetyl

Table of DNA-Sequences corresponding to Examples 1-14

TABLE 5

Examples 1-2, n = 8

| | R¹ | Cys | P1 | P2 | P3 | P4 | P5 | P6 | P7 | P8 | Cys | R² |
|---|---|---|---|---|---|---|---|---|---|---|---|---|
| SeqID No: 28 | | TGC | AAA | TGG | TTC | CTG | GCG | CTA | TAT | GCG | TGC | |
| SeqID No: 29 | GAA ACC | TGC | AAA | TGG | TTC | CTG | GCG | CAT | TAT | GCG | TGC | ACC AAA |

TABLE 6

Examples 3-9, n = 10

| | R¹ Cys P1 P2 P3 P4 P5 P6 P7 P8 P9 P10 Cys R² |
|---|---|
| SeqID No: 30 | TGC ACC AAA TGG TTC AGC AAC CAT TAT CAG ACC TGC |
| SeqID No: 31 | GAA ACC TGC ACC AAA TGG TTC AGC AAC CAT TAT CAG ACC TGC ACC AAA |
| SeqID No: 32 | TGC ACC AAA TGG TTC CTG GCG CAT TAT GCG ACC TGC |
| SeqID No: 33 | CTG GAA TGC ACC AAA TGG TTC CTG GCG CAT TAT GCG ACC TGC AAA GTT |
| SeqID No: 34 | AAC GGT TGC ACC AAA TGG TTC CTG GCG CAT TAT GCG ACC TGC AAA GTT |
| SeqID No: 35 | GGT GGT TGC ACC AAA TGG TTC CTG GCG CAT TAT GCG ACC TGC GGC GGT |
| SeqID No: 36 | GAA ACC TGC ACC AAA TGG TTC CTG GCG CAT TAT GCG ACC TGC ACC AAA |

TABLE 7

Examples 10-12 n = 10

| | R¹ Cys P1 P2 P3 P4 P5 P6 P7 P8 P9 P10 Cys R² |
|---|---|
| SeqID No: 37 | GAA CTG AAA TGC ACC AAA TGG TTC AGC AAC CAT TAT CAG ACC TGC GAA GTT AAA |
| SeqID No: 38 | AAA GTT GGT TGC ACC AAA TGG TTC CTG GCG CAT TAT GCG ACC TGC GGT CTG GAA |
| SeqID No: 39 | GGT GGT GGC TGC ACC AAA TGG TTC CTG GCG CAT TAT GCG ACC TGC GGC GGT GGT |

TABLE 8

Examples 13-14, n = 12

| Seq. ID | R¹ Cys P1 P2 P3 P4 P5 P6 P7 P8 P9 P10 P11 P12 Cys R² |
|---|---|
| SeqID No 40 | TGC GGT ACC AAA TGG TTC AGC AAC CAT TAT CAG ACC GGT TGC |
| SeqID No 41 | GAA ACC TGC GGT ACC AAA TGG TTC AGC AAC CAT TAT CAG ACC GGT TGC ACC AAA |

TABLE 9

Example 15, n = 10, DNA Sequence and translated peptide sequence of a randomized template fixed β-hairpin mimetic Phage library

| Example | Seq. ID | R¹ | Cys | P1 | P2 | P3 | P4 | P5 |
|---|---|---|---|---|---|---|---|---|
| Ex. 15 | SeqID No: 42 | GAA | ACC | TGC | NNK | NNK | NNK | CGT | GGT |
| | SeqID No: 43 | Glu | Thr | Cys | X | X | X | Arg | Gly |

Example 15, n = 10, DNA Sequence and translated peptide sequence of a randomized template fixed β-hairpin mimetic Phage library

| Example | Seq. ID | P6 | P7 | P8 | P9 | P10 | Cys | R² |
|---|---|---|---|---|---|---|---|---|
| Ex. 15 | SeqID No: 42 | GAC | NNK | NNK | NNK | NNK | TGC | ACC AAA |
| | SeqID No: 43 | Asp | X | X | X | X | Cys | Thr Lys |

X: randomized amino acid positions
Cysteines are linked by a disulfide bridge

The invention claimed is:

1. A method of screening for template-fixed hairpin beta-mimetics having a template that conformationally stabilizes a beta-hairpin and which is capable of binding to a specific binding partner, comprising the steps of
   a) providing a library of template-fixed beta-hairpin mimetics;
   b) contacting the library of step a) with the binding partner;
   c) selecting from the library peptides capable of forming a non-covalent complex with the binding partner; and
   d) optionally isolating the peptides or determining their sequence by DNA-analysis, wherein the library of template-fixed beta-hairpin mimetics comprises compounds of the general formula $R^1$-Cys-Z-Cys-$R^2$ (I), in which
   the two Cys residues form a disulfide bridge,
   $R^1$ and $R^2$ comprise Glu-Thr and Thr-Lys; or Lys-Thr and Thr-Glu; or Thr-Glu and Lys-Thr; or Thr-Lys and Glu-Thr; or Leu-Glu and Lys-Val; or Val-Lys and Glu-Leu; or Glu-Leu and Val-Lys; or Lys-Leu and Val-Glu; or Glu-Leu-Lys and Glu-Val-Lys; or Lys-Val-Glu and Lys-Leu-Glu; or Leu-Glu-Lys and Glu-Lys-Val; or Val-Lys-Glu and Lys-Glu-Leu; or Glu-Lys-Leu and Val-Glu-Lys; or Lys-Glu-Val and Leu-Lys-Glu; or Lys-Glu-Leu and Val-Lys-Glu; or Glu-Lys-Val and Leu-Glu-Lys, and
   Z is -Lys-Trp-Phe-Ser-Asn-His-Tyr-Gln-[SEQ ID NO:23]; or -Phe-Leu-Ala-His-Tyr-Ala-[SEQ ID NO:24].

2. A method according to claim 1, wherein the binding partner is selected from the group consisting of an antibody; an enzyme; a ligand; and a receptor.

3. A method of screening for template-fixed hairpin beta-mimetics having a template that conformationally stabilizes a beta-hairpin and which is capable of binding to a specific binding partner, comprising the steps of
   a) providing a library of template-fixed beta-hairpin mimetics;
   b) contacting the library of step a) with the binding partner;
   c) selecting from the library peptides capable of forming a non-covalent complex with the binding partner; and
   d) optionally isolating the peptides or determining their sequence by DNA-analysis, wherein the library of template-fixed beta-hairpin mimetics comprises compounds,
   wherein said compounds in said library are peptides having a sequence selected from the group consisting of SEQ ID NO: 9, SEQ ID NO: 11, SEQ ID NO: 13, SEQ ID NO: 16, SEQ ID NO: 17, and SEQ ID NO: 21.

* * * * *

SEQUENCE LISTING

<160> NUMBER OF SEQ ID NOS: 44

<210> SEQ ID NO 1
<211> LENGTH: 4
<212> TYPE: PRT
<213> ORGANISM: Artificial Sequence
<220> FEATURE:
<223> OTHER INFORMATION: Key sequence known to occur in Platelet-Derived
      Growth Factor (PDGF), see Ross, R.; Raines, E. W.; Bowden-Pope,
      D.F.; Cell, 1986, 46, 155-159.

<400> SEQUENCE: 1

Val Arg Lys Lys
1

<210> SEQ ID NO 2
<211> LENGTH: 4
<212> TYPE: PRT
<213> ORGANISM: Artificial Sequence
<220> FEATURE:
<223> OTHER INFORMATION: Key sequence known to occur in Vasointestinal
      Peptide (VIP) showing neuroprotective properties against
      beta-amyloid neurotoxicity, see Proc. Natl. Am. Soc. USA, 1996,
      96, 4143-4148.

```
<400> SEQUENCE: 2

Lys Lys Tyr Leu
1

<210> SEQ ID NO 3
<211> LENGTH: 4
<212> TYPE: PRT
<213> ORGANISM: Artificial Sequence
<220> FEATURE:
<223> OTHER INFORMATION: Key sequence known to occur in integrin
      alpha.sub4 beta.sub1, see Europ. J. Biol., 1996, 242, 352-362 and
      Int. J. Pept. Prot. Res., 1996, 47, 427-436.

<400> SEQUENCE: 3

Trp Leu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Key sequence known to occur in Factor Xa
      inhibitors, see Al Obeidis, F.; Ostrem, J. A.; Drug Discovery
      Today, 1998, 3, 223-231.

<400> SEQUENCE: 4

Tyr Ile Arg Leu Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Key sequence known to occur in laminine, see
      EMBO. J., 1984, 3, 1463.

<400> SEQUENCE: 5

Tyr Ile Gly Ser Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Key sequence known to occur in important
      physiologically active peptides, see Cell, 1987, 88, 989.

<400> SEQUENCE: 6

Ile Lys Val Ala Val
1               5

<210> SEQ ID NO 7
<211> LENGTH: 6
<212> TYPE: PRT
<213> ORGANISM: Artificial Sequence
<220> FEATURE:
<223> OTHER INFORMATION: Key sequence known to occur in important
      physiologically active peptides, see J. Biol. Chem., 1998, 273,
      11001-11006 and 11007-11011.
<220> FEATURE:
<221> NAME/KEY: misc_feature
<222> LOCATION: (4)..(5)
<223> OTHER INFORMATION: Xaa can be any naturally occurring amino acid

<400> SEQUENCE: 7
```

```
Pro Pro Arg Xaa Xaa Trp
1               5

<210> SEQ ID NO 8
<211> LENGTH: 10
<212> TYPE: PRT
<213> ORGANISM: Artificial Sequence
<220> FEATURE:
<223> OTHER INFORMATION: Hairpin mimetic derived from the general
      formula Cys-Z-Cys wherein the alpha amino group of the first amino
      acid is acetylated and wherein Z consists of 8 amino acids.
<220> FEATURE:
<221> NAME/KEY: DISULFID
<222> LOCATION: (1)..(10)
<220> FEATURE:
<221> NAME/KEY: MOD_RES
<222> LOCATION: (1)..(1)
<223> OTHER INFORMATION: ACETYLATION

<400> SEQUENCE: 8

Cys Lys Trp Phe Leu Ala His Tyr Ala Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 8 amino acids, and
      wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(12)

<400> SEQUENCE: 9

Glu Thr Cys Lys Trp Phe Leu Ala His Tyr Ala Cys Thr Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: hairpin mimetic derived from the general
      formula Cys-Z-Cys wherein the alpha amino group of the first amino
      acid is acetylated and wherein Z consists of 10 amino acids.
<220> FEATURE:
<221> NAME/KEY: DISULFID
<222> LOCATION: (1)..(12)
<220> FEATURE:
<221> NAME/KEY: MOD_RES
<222> LOCATION: (1)..(1)
<223> OTHER INFORMATION: ACETYLATION

<400> SEQUENCE: 10

Cys Thr Lys Trp Phe Ser Asn His Tyr Gln Thr Cys
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
```

```
          and wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(14)

<400> SEQUENCE: 11

Glu Thr Cys Thr Lys Trp Phe Ser Asn His Tyr Gln Thr Cys Thr Lys
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Hairpin mimetic derived from the general
      formula Cys-Z-Cys wherein the alpha amino group of the first amino
      acid is acetylated and wherein Z consists of 10 amino acids.
<220> FEATURE:
<221> NAME/KEY: DISULFID
<222> LOCATION: (1)..(12)
<220> FEATURE:
<221> NAME/KEY: MOD_RES
<222> LOCATION: (1)..(1)
<223> OTHER INFORMATION: ACETYLATION

<400> SEQUENCE: 12

Cys Thr Lys Trp Phe Leu Ala His Tyr Ala Thr Cys
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(14)

<400> SEQUENCE: 13

Leu Glu Cys Thr Lys Trp Phe Leu Ala His Tyr Ala Thr Cys Lys Val
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(14)

<400> SEQUENCE: 14
```

```
Asn Gly Cys Thr Lys Trp Phe Leu Ala His Tyr Ala Thr Cys Lys Val
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(14)

<400> SEQUENCE: 15

Gly Gly Cys Thr Lys Trp Phe Leu Ala His Tyr Ala Thr Cys Gly Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 2 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (3)..(14)

<400> SEQUENCE: 16

Glu Thr Cys Thr Lys Trp Phe Leu Ala His Tyr Ala Thr Cys Thr Lys
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 3 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (4)..(15)

<400> SEQUENCE: 17

Glu Leu Lys Cys Thr Lys Trp Phe Ser Asn His Tyr Gln Thr Cys Glu
1               5                   10                  15

Val Lys

<210> SEQ ID NO 18
<211> LENGTH: 18
<212> TYPE: PRT
<213> ORGANISM: Artificial Sequence
```

```
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 3 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (4)..(15)

<400> SEQUENCE: 18

Lys Val Gly Cys Thr Lys Trp Phe Leu Ala His Tyr Ala Thr Cys Gly
1               5                   10                  15

Leu Glu

<210> SEQ ID NO 19
<211> LENGTH: 18
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 10 amino acids,
      and wherein both R1 and R2 consist of 3 amino acids.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (4)..(15)

<400> SEQUENCE: 19

Gly Gly Gly Cys Thr Lys Trp Phe Leu Ala His Tyr Ala Thr Cys Gly
1               5                   10                  15

Gly Gly

<210> SEQ ID NO 20
<211> LENGTH: 14
<212> TYPE: PRT
<213> ORGANISM: Artificial Sequence
<220> FEATURE:
<223> OTHER INFORMATION: Hairpin mimetic derived from the general
      formula Cys-Z-Cys wherein the alpha amino group of the first amino
      acid is acetylated and wherein Z consists of 12 amino acids.
<220> FEATURE:
<221> NAME/KEY: DISULFID
<222> LOCATION: (1)..(14)
<220> FEATURE:
<221> NAME/KEY: MOD_RES
<222> LOCATION: (1)..(1)
<223> OTHER INFORMATION: ACETYLATION

<400> SEQUENCE: 20

Cys Gly Thr Lys Trp Phe Ser Asn His Tyr Gln Thr Gly Cys
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Hairpin mimetic derived from the general
      formula R1-Cys-Z-Cys-R2 wherein the alpha amino group of the first
      amino acid is acetylated, wherein Z consists of 12 amino acids,
      and wherein both R1 and R2 consist of 2 amino acids.
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: DISULFID
<222> LOCATION: (3)..(16)

<400> SEQUENCE: 21

Glu Thr Cys Gly Thr Lys Trp Phe Ser Asn His Tyr Gln Thr Gly Cys
1               5                   10                  15

Thr Lys

<210> SEQ ID NO 22
<211> LENGTH: 8
<212> TYPE: PRT
<213> ORGANISM: Artificial Sequence
<220> FEATURE:
<223> OTHER INFORMATION: Core peptide sequence Z taken from the CDR L3
      loop of an antibody described in Jiang, L. et al., Chimia,
      2000, 54, 558-563.

<400> SEQUENCE: 22

Leu Trp Tyr Ser Asn His Trp Val
1               5

<210> SEQ ID NO 23
<211> LENGTH: 8
<212> TYPE: PRT
<213> ORGANISM: Artificial Sequence
<220> FEATURE:
<223> OTHER INFORMATION: Modified core peptide sequence Z derived from
      core peptide sequence with the SEQ ID NO:22 containing a
      stabilizing beta-turn and a beta-sheet sequence according to Chou,
      P. Y., Fasman, G. D., J. Mol. Biol, 1977, 115, 135-175.

<400> SEQUENCE: 23

Lys Trp Phe Ser Asn His Tyr Gln
1               5

<210> SEQ ID NO 24
<211> LENGTH: 6
<212> TYPE: PRT
<213> ORGANISM: Artificial Sequence
<220> FEATURE:
<223> OTHER INFORMATION: Core peptide sequence Z constructed from
      peptide with the SEQ ID NO:25.

<400> SEQUENCE: 24

Phe Leu Ala His Tyr Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Oligopeptide which does not contain a dedicated
      stabilizing beta-turn sequence or a beta-sheet sequence according
      to Chou, P. Y., Fasman, G. D., J. Mol. Biol, 1977, 115, 135-175.

<400> SEQUENCE: 25

Leu Trp Tyr Ser Asn His Trp Val Lys Trp
1               5                   10

<210> SEQ ID NO 26
<211> LENGTH: 39
<212> TYPE: DNA
<213> ORGANISM: Artificial Sequence
<220> FEATURE:
```

```
<223> OTHER INFORMATION: Oligonucleotide No. 1 used to construct insert
      DNA coding for template fixed hairpin mimetic of SEQ ID NO:10 and
      used to construct insert DNA coding for randomized library
      template fixed beta-hairpin mimetics having sequences according to
      SEQ ID NO:42.

<400> SEQUENCE: 26
catgcccggg tacctttcta ttctcactct gaaacctgc                              39

<210> SEQ ID NO 27
<211> LENGTH: 84
<212> TYPE: DNA
<213> ORGANISM: Artificial Sequence
<220> FEATURE:
<223> OTHER INFORMATION: Oligonucleotide No. 2 used to construct insert
      DNA coding for template fixed hairpin mimetic of SEQ ID NO:10.

<400> SEQUENCE: 27
catgtttcgg ccgagccacc acctttggtg caggtctgat aatggttgct gaaccatttg      60
gtgcaggttt cagagtgaga atag                                             84

<210> SEQ ID NO 28
<211> LENGTH: 30
<212> TYPE: DNA
<213> ORGANISM: Artificial Sequence
<220> FEATURE:
<223> OTHER INFORMATION: DNA sequence coding for the peptide shown in
      SEQ ID NO:8.

<400> SEQUENCE: 28
tgcaaatggt tcctggcgca ttatgcgtgc                                       30

<210> SEQ ID NO 29
<211> LENGTH: 42
<212> TYPE: DNA
<213> ORGANISM: Artificial Sequence
<220> FEATURE:
<223> OTHER INFORMATION: DNA sequence coding for the peptide shown in
      SEQ ID NO:9.

<400> SEQUENCE: 29
gaaacctgca aatggttcct ggcgcattat gcgtgcacca aa                         42

<210> SEQ ID NO 30
<211> LENGTH: 36
<212> TYPE: DNA
<213> ORGANISM: Artificial Sequence
<220> FEATURE:
<223> OTHER INFORMATION: DNA sequence coding for the peptide shown in
      SEQ ID NO:10.

<400> SEQUENCE: 30
tgcaccaaat ggttcagcaa ccattatcag acctgc                                36

<210> SEQ ID NO 31
<211> LENGTH: 48
<212> TYPE: DNA
<213> ORGANISM: Artificial Sequence
<220> FEATURE:
<223> OTHER INFORMATION: DNA sequence coding for the peptide shown in
      SEQ ID NO:11.

<400> SEQUENCE: 31
gaaacctgca ccaaatggtt cagcaaccat tatcagacct gcaccaaa                   48

<210> SEQ ID NO 32
```

```
<211> LENGTH: 36
<212> TYPE: DNA
<213> ORGANISM: Artificial Sequence
<220> FEATURE:
<223> OTHER INFORMATION: DNA sequence coding for the peptide shown in
      SEQ ID NO:12.

<400> SEQUENCE: 32
tgcaccaaat ggttcctggc gcattatgcg acctgc                                  36

<210> SEQ ID NO 33
<211> LENGTH: 48
<212> TYPE: DNA
<213> ORGANISM: Artificial Sequence
<220> FEATURE:
<223> OTHER INFORMATION: DNA sequence coding for the peptide shown in
      SEQ ID NO:13.

<400> SEQUENCE: 33
ctggaatgca ccaaatggtt cctggcgcat tatgcgacct gcaaagtt                     48

<210> SEQ ID NO 34
<211> LENGTH: 48
<212> TYPE: DNA
<213> ORGANISM: Artificial Sequence
<220> FEATURE:
<223> OTHER INFORMATION: DNA sequence coding for the peptide shown in
      SEQ ID NO:14.

<400> SEQUENCE: 34
aacggttgca ccaaatggtt cctggcgcat tatgcgacct gcaaagtt                     48

<210> SEQ ID NO 35
<211> LENGTH: 48
<212> TYPE: DNA
<213> ORGANISM: Artificial Sequence
<220> FEATURE:
<223> OTHER INFORMATION: DNA sequence coding for the peptide shown in
      SEQ ID NO:15.

<400> SEQUENCE: 35
ggtggttgca ccaaatggtt cctggcgcat tatgcgacct gcggcggt                     48

<210> SEQ ID NO 36
<211> LENGTH: 48
<212> TYPE: DNA
<213> ORGANISM: Artificial Sequence
<220> FEATURE:
<223> OTHER INFORMATION: DNA sequence coding for the peptide shown in
      SEQ ID NO:16.

<400> SEQUENCE: 36
gaaacctgca ccaaatggtt cctggcgcat tatgcgacct gcaccaaa                     48

<210> SEQ ID NO 37
<211> LENGTH: 54
<212> TYPE: DNA
<213> ORGANISM: Artificial Sequence
<220> FEATURE:
<223> OTHER INFORMATION: DNA sequence coding for the peptide shown in
      SEQ ID NO:17.

<400> SEQUENCE: 37
gaactgaaat gcaccaaatg gttcagcaac cattatcaga cctgcgaagt taaa              54

<210> SEQ ID NO 38
<211> LENGTH: 54
```

-continued

```
<212> TYPE: DNA
<213> ORGANISM: Artificial Sequence
<220> FEATURE:
<223> OTHER INFORMATION: DNA sequence coding for the peptide shown in
      SEQ ID NO:18.

<400> SEQUENCE: 38
aaagttggtt gcaccaaatg gttcctggcg cattatgcga cctgcggtct ggaa           54

<210> SEQ ID NO 39
<211> LENGTH: 54
<212> TYPE: DNA
<213> ORGANISM: Artificial Sequence
<220> FEATURE:
<223> OTHER INFORMATION: DNA sequence coding for the peptide shown in
      SEQ ID NO:19.

<400> SEQUENCE: 39
ggtggtggct gcaccaaatg gttcctggcg cattatgcga cctgcggcgg tggt           54

<210> SEQ ID NO 40
<211> LENGTH: 42
<212> TYPE: DNA
<213> ORGANISM: Artificial Sequence
<220> FEATURE:
<223> OTHER INFORMATION: DNA sequence coding for the peptide shown in
      SEQ ID NO:20.

<400> SEQUENCE: 40
tgcggtacca aatggttcag caaccattat cagaccggtt gc                       42

<210> SEQ ID NO 41
<211> LENGTH: 54
<212> TYPE: DNA
<213> ORGANISM: Artificial Sequence
<220> FEATURE:
<223> OTHER INFORMATION: DNA sequence coding for the peptide shown in
      SEQ ID NO:21.

<400> SEQUENCE: 41
gaaacctgcg gtaccaaatg gttcagcaac cattatcaga ccggttgcac caaa          54

<210> SEQ ID NO 42
<211> LENGTH: 48
<212> TYPE: DNA
<213> ORGANISM: Artificial Sequence
<220> FEATURE:
<223> OTHER INFORMATION: DNA sequence of randomized template fixed
      beta-hairpin mimetic Phage library.
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
```

-continued

<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 42
gaaacctgcn nknnknnkcg tggtgacnnk nnknnknnkt gcaccaaa                48

<210> SEQ ID NO 43
<211> LENGTH: 16
<212> TYPE: PRT
<213> ORGANISM: Artificial Sequence
<220> FEATURE:
<223> OTHER INFORMATION: Translated protein sequence of a randomized
      template fixed beta-hairpin mimetic phage library
<220> FEATURE:
<221> NAME/KEY: DISULFID
<222> LOCATION: (3)..(14)
<220> FEATURE:
<221> NAME/KEY: MISC_FEATURE
<222> LOCATION: (4)..(6)
<223> OTHER INFORMATION: Xaa can be any naturally occurring amino acid
<220> FEATURE:
<221> NAME/KEY: MISC_FEATURE
<222> LOCATION: (10)..(13)
<223> OTHER INFORMATION: Xaa can be any naturally occurring amino acid

<400> SEQUENCE: 43

Glu Thr Cys Xaa Xaa Xaa Arg Gly Asp Xaa Xaa Xaa Xaa Cys Thr Lys
1               5                   10                  15

<210> SEQ ID NO 44
<211> LENGTH: 84
<212> TYPE: DNA
<213> ORGANISM: Artificial Sequence
<220> FEATURE:
<223> OTHER INFORMATION: Oligonucleotide No. 3 used to construct insert
      DNA coding for randomized library template fixed beta-hairpin
      mimetics having sequences according to SEQ ID NO:42.
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 44

```
catgtttcgg ccgagccacc acctttggtg camnnmnnmn nmnngtcacc acgmnnmnnm    60
nngcaggttt cagagtgaga atag                                            84
```